US008222217B2

(12) United States Patent
Ghigo et al.

(10) Patent No.: US 8,222,217 B2
(45) Date of Patent: Jul. 17, 2012

(54) UNACYLATED GHRELIN AS THERAPEUTIC AGENT IN THE TREATMENT OF METABOLIC DISORDERS

(75) Inventors: Ezio Ghigo, Turin (IT); Riccarda Granata, Turin (IT); Aart Jan Van Der Lely, Bergschenhoek (NL)

(73) Assignee: Alize Pharma SAS, Ecully (FR)

( * ) Notice: Subject to any disclaimer, the term of this patent is extended or adjusted under 35 U.S.C. 154(b) by 0 days.

(21) Appl. No.: 12/130,615

(22) Filed: May 30, 2008

(65) Prior Publication Data

US 2008/0312133 A1 Dec. 18, 2008

Related U.S. Application Data

(60) Provisional application No. 60/941,186, filed on May 31, 2007.

(51) Int. Cl.
*A61K 38/00* (2006.01)
*A61K 38/08* (2006.01)
*A61K 38/12* (2006.01)
*A61P 3/10* (2006.01)

(52) U.S. Cl. .......... 514/21.8; 514/6.7; 514/6.8; 514/6.9; 514/21.1

(58) Field of Classification Search ................ None
See application file for complete search history.

(56) References Cited

U.S. PATENT DOCUMENTS

| | | | |
|---|---|---|---|
| 5,037,743 A | 8/1991 | Welch et al. | |
| 5,143,830 A | 9/1992 | Holland et al. | |
| 6,271,198 B1 * | 8/2001 | Braisted et al. | 514/3.8 |
| 6,967,237 B2 * | 11/2005 | Bednarek | 530/300 |
| 7,485,620 B2 | 2/2009 | Ghigo et al. | |
| 7,666,833 B2 | 2/2010 | Ghigo et al. | |
| 7,825,090 B2 | 11/2010 | Ghigo et al. | |
| 2005/0080007 A1 * | 4/2005 | Ghigo et al. | 514/12 |

FOREIGN PATENT DOCUMENTS

| | | |
|---|---|---|
| CA | 2470235 | 6/2003 |
| CA | 2471879 | 11/2003 |
| CA | 2543507 | 5/2005 |
| EP | 2067481 | 6/2009 |
| WO | WO-01/56592 | 8/2001 |
| WO | WO-01/87335 | 11/2001 |
| WO | 01/92292 A2 | 12/2001 |
| WO | 02/060472 A1 | 8/2002 |
| WO | WO-03/051389 A | 6/2003 |
| WO | WO 2005/039624 A1 | 5/2005 |
| WO | WO-2006/045319 A | 5/2006 |
| WO | WO 2007/126792 A1 | 11/2007 |
| WO | WO 2008/145749 A1 | 12/2008 |
| WO | WO-2009/071283 | 6/2009 |

OTHER PUBLICATIONS

Salehi et al., Regulatory Peptides 118: 143-150, 2006.*
Makino et al., Biopolymers, 79: 238-247, 2005.*
Wells, 1990, Biochemistry 29:8509-8517.*
Soares, et al., "Ghrelin, des-acyl ghrelin and obestatin: three pieces of the same puzzle." Peptides Jul. 2008, vol. 29, No. 7, pp. 1255-1270.
Atkinson et al., "Type 1 Diabetes: New Perspectives on Disease Pathogenesis and Treatment" The Lancet 358: pp. 221-229, 2001.
Florez J. "The Genetics of Type 2 Diabetes: A Realistic Appraisal in 2008" C., J. Clin. End. Metab. 93: pp. 4633-4642, 2008.
Kojima M, Hosoda H, Date Y, Nakazato M, Matsuo H, Kangawa K; (1999) Ghrelin is a growth-hormone-releasing acylated peptide from stomach. Nature 402:656-660.
Van der Lely AJ, Tschop M, Heiman ML, Ghigo E; (2004) Biological, physiological, pathophysiological, and pharmacological aspects of ghrelin. Endocr Rev 25:426-457.
Gauna C, Delhanty PJ, Hofland LJ, Janssen JA, Broglio F, Ross RJ, Ghigo E, van der Lely AJ; (2005) Ghrelin stimulates, whereas desoctanoyl ghrelin inhibits, glucose output by primary hepatocytes. J Clin Endocrinol Metab 90:1055-1060.
Granata R, Settanni F, Biancone L, Trovato L, Nano R, Bertuzzi F, Destefanis S, Annunziata M, Martinetti M, Catapano F, Ghe C, Isgaard J, Papotti M, Ghigo E, Muccioli G; (2007) Acylated and unacylated ghrelin promote proliferation and inhibit apoptosis of pancreatic b cells and human islets involvement of CAMP/PKA, ERK1/2 and PI3K/AKT signaling. Endocrinology 148:512-529.
Merglen A, Theander S, Rubi B, Chaffard G, Wollheim CB, Maechler P.; (2004) Glucose sensitivity and metabolism-secretion coupling studied during two-year continuous culture in INS-1E insulinoma cells. Endocrinology 145:667-678.
Broglio F, Gottero C, Prodam F, Gauna C, Muccioli G, Papotti M, Abribat T, Van Der Lely AJ, Ghigo E; (2004) Non-acylated ghrelin counteracts the metabolic but not the neuroendocrine response to acylated ghrelin in humans. J Clin Endocrinol Metab 89:3062-3065.
Asakawa A, Inui A, Fujimiya M et al.; (2005) Stomach regulates energy balance via acylated ghrelin and desacyl ghrelin. Gut 54:18-24.
Baldanzi G, Filigheddu N, Cutrupi S, Catapano F, Bonissoni S, Fubini A, Malan D, Baj G, Granata R, Broglio F, Papotti M, Surico N, Bussolino F, Isgaard J, Deghenghi R, Sinigaglia F, Prat M, Muccioli G, Ghigo E, Graziani A; (2002) Ghrelin and des-acyl ghrelin inhibit cell death in cardiomyocytes and endothelial cells through ERK1/2 and PI 3-kinase/AKT. J Cell Biol 159:1029-1037.
Date Y, Nakazato M, Hashiguchi S, Dezaki K, Mondal MS, Hosoda H, Kojima M, Kangawa K, Arima T, Matsuo H, Yada T, Matsukura S; (2002) Ghrelin is present in pancreatic alpha-cells of humans and rats and stimulates insulin secretion. Diabetes 51:124-129.
Delhanty PJ, van Koetsveld PM, Gauna C, van de Zande B, Vitale G, Hofland LJ, van der Lely AJ; (2007) Ghrelin and its unacylated isoform stimulate the growth of adrenocortical tumor cells via an anti-apoptotic pathway. Am J Physiol Endocrinol Metab. 293:E302-309.
Dezaki K, Kakei M, Yada T; (2007) Ghrelin uses Galphai2 and activates voltage-dependent K+ channels to attenuate glucose-induced Ca2+ signaling and insulin release in islet beta-cells: novel signal transduction of ghrelin. Diabetes. 56:2319-2327.
Filigheddu N, Gnocchi VF, Coscia M, Cappelli M, Porporato PE, Taulli R, Traini S, Baldanzi G, Chianale F, Cutrupi S, Arnoletti E, Ghè C, Fubini A, Surico N, Sinigaglia F, Ponzetto C, Muccioli G, Crepaldi T, Graziani A; (2007) Ghrelin and des-acyl ghrelin promote differentiation and fusion of C2C12 skeletal muscle cells. Mol Biol Cell. 18:986-994.

(Continued)

Primary Examiner — Gyan Chandra
(74) *Attorney, Agent, or Firm* — Fish & Richardson P.C.

(57) ABSTRACT

An isolated polypeptide comprising any amino acid fragment of unacylated ghrelin or any analog thereof, wherein the polypeptide has an activity selected from the group consisting of a) decreasing blood glucose levels; b) increasing insulin secretion an/or sensitivity; c) binding to insulin-secreting cells; and d) promoting survival of insulin-secreting cells. As well as the use of the polypeptide in the treatment of a disorder associated with impaired glucose metabolism.

28 Claims, 33 Drawing Sheets

OTHER PUBLICATIONS

Gauna C, Kiewiet RM, Janssen JA, van de Zande B, Delhanty PJ, Ghigo E, Hofland LJ, Themmen AP, van der Lely AJ; (2007) Unacylated ghrelin acts as a potent insulin secretagogue in glucose-stimulated conditions. Am J Physiol Endocrinol Metab 293:E697-704.

Granata R, Settanni F, Trovato L, Destefanis S, Gallo D, Martinetti M, Ghigo E, Muccioli G; (2006) Unacylated as well as acylated ghrelin promotes cell survival and inhibit apoptosis in HIT-T15 pancreatic beta-cells. J Endocrinol Invest 29:RC19-22.

Granata R, Settanni F, Gallo D, Trovato L, Biancone L, Cantaluppi V, Nano R, Annunziata M, Campiglia P, Arnoletti E, Ghè C, Volante M, Papotti M, Muccioli G, Ghigo E; (2008) Obestatin promotes survival of pancreatic β-cells and human islets and induces expression of genes involved in the regulation of -cell mass and function. Diabetes 57:967-79.

Mandrup-Poulsen T; (2001) beta-cell apoptosis: stimuli and signaling. Diabetes 50:S58-63.

Muccioli G, Pons N, Ghe C, Catapano F, Granata R, Ghigo E; (2004) Ghrelin and des-acyl ghrelin both inhibit isoproterenol-induced lipolysis in rat adipocytes via a non-type la growth hormone secretagogue receptor. Eur J Pharmacol 498:27-35.

Park S, Dong X, Fisher TL, Dunn S, Omer AK, Weir G, White MF; (2006) Exendin-4 uses Irs2 signaling to mediate pancreatic beta cell growth and function. J Biol Chem 281:1159-1168.

Prado CL, Pugh-Bernard AE, Elghazi L, Sosa-Pineda B, Sussel L; (2004) Ghrelin cells replace insulin-producing beta cells in two mouse models of pancreas development. Proc Natl Acad Sci USA 101:2924-2929.

Santerre RF, Cook RA, Crisel RM, Sharp JD, Schmidt RJ, Williams DC, Wilson CP; (1981) Insulin synthesis in a clonal cell line of simian virus 40-transformed hamster pancreatic beta cells. Proc Natl Acad Sci USA 78:4339-4343.

Wajchenberg BL; (2007) beta-cell failure in diabetes and preservation by clinical treatment. Endocr Rev. 28:187-218.

Wierup N, Svensson H, Mulder H, Sundler F; (2002) The ghrelin cell: a novel developmentally regulated islet cell in the human pancreas. Regul Pept 107:63-69.

Zhang JV, Ren PG, Avsian-Kretchmer O, Luo CW, Rauch R, Klein C, Hsueh AJ; (2005) Obestatin, a peptide encoded by the ghrelin gene, opposes ghrelin's effects on food intake. Science 310:996-999.

Irako T, Akamizu T, Hosoda H, Iwakura H, Ariyasu H, Tojo K, Tajima N, Kangawa K; (2006) Ghrelin prevents development of diabetes at adult age in streptozotocin-treated newborn rats. Diabetologia 49:1264-1273.

Portha B, Levacher C, Picon L, Rosselin G.; (1974) Diabetogenic effect of streptozotocin in the rat during the perinatal period. Diabetes 23:889-895.

Tourrel C, Bailbé D, Meile MJ, Kergoat M, Portha B; (2001) Glucagon-like peptide-1 and exendin-4 stimulate beta-cell neogenesis in streptozotocin-treated newborn rats resulting in persistently improved glucose homeostasis at adult age. Diabetes 50:1562-1570.

Menahan LA; (1983) Age-related changes in lipid and carbohydrate metabolism of the genetically obese mouse. Metabolism 32:172-178.

Hayashi T, Boyko EJ, McNeely MJ, Leonetti DL, Kahn SE, Fujimoto WY; (2008) Visceral Adiposity, not Abdominal Subcutaneous Fat Area, Is Associated with an Increase in Future Insulin Resistance in Japanese Americans. Diabetes May; 57(5):1269-75. Epub Feb. 25, 2008.

Hamdy O, Porramatikul S, Al-Ozairi E; (2006) Metabolic obesity: the paradox between visceral and subcutaneous fat. Curr Diabetes Rev 2:367-373.

Prodam, et al., Unacylated Ghrelin (UAG) Enhances the Early Insulin Response to Meal, Improves Glucose Metabolism and Decrease Free Faty Acids Levels in Health Volumteers, Abstract and poster presented at European Congress of Endocrinology, Budapest, from Apr. 28, 2007 to May 2, 2007.

Cassoni, et al., Identification, Characterization, and Biological Activity of Specific Receptors for Natural (Ghrelin) and Synthetic Growth Hormone Secretagogues and Analogs in Human Breast Carcinomas and Cell Lines, The Journal of Clinical Endocrinology & Metabolism, vol. 86, No. 4, pp. 1738-1744, 2001.

Toshinai, et al., Upregulation of Ghrelin Expression in the Stomach upon Fasting, Insulin-Induced Hypoglycemia, and Leptin Administration, Biochemical and Biophysical Research Communications, vol. 281, pp. 1220-1225, 2001.

Mickle and Cutting, "Genotype-Phenotype Relationships in Cystic Fibrosis", Med. Clin. North Am., 2000, vol. 84(3), p. 597-607.

Adelhorst, et al., "Structure-Activity Studies of Glucagon-like Peptide-1," J. Biol. Chem. 269: 6275-6278, 1994.

Marzullo, et al., "The Relationship between Active Ghrelin Levels and Human Obesity Involves Alterations in Resting Energy Expenditure," J. Clin. Endocr. Metab. 89: 936-939, 2004.

Granata, et al., Acylated and unacylate ghrelin promote proliferation and inhibit serum stravation- and cytokine-induced apoptosis of pancreatic beta cells through cAMP/PKA, ERK 1/2 and PI3K/Akt, Abstract and poster presented at Meeting of the Endocrine Society, Boston, from Jun. 24, 2006.

Pöykkö, et al., Low Plasma Ghrelin is Associated With Insulin Resistance, Hypertension, and the Prevalence of Type 2 Diabetes, Diabetes, vol. 52, pp. 2546-2553, Oct. 2003.

Li et al Cardioprotective effects of ghrelin and des-ghrelin on myocardial injury induced by isoproterenol in rats, Acta Pharmacological Sinica, 27:527-535 (2006).

International Search Report mailed on Jan. 25, 2010 in connection with International Patent Application PCT/EP2009/057263 (WO 2009/150214 A3).

* cited by examiner

UNACYLATED GHRELIN AS THERAPEUTIC AGENT IN THE TREATMENT OF METABOLIC DISORDERS

CROSS-REFERENCE TO RELATED APPLICATIONS

This application claims the benefit of and priority to U.S. provisional patent application No. 60/941,186 filed May 31, 2007, the content of which is herein incorporated by reference.

REFERENCE TO SEQUENCE LISTING

Pursuant to 37 C.F.R. 1.821(c), a sequence listing is submitted herewith as an ASCII compliant text file named "Sequence Listing.txt" which was created on Mar. 10, 2011 and has a size of 5324 bytes. The content of the aforementioned file named "Sequence listing.txt" is hereby incorporated by reference in its entirety.

FIELD OF THE INVENTION

This invention relates to unacylated ghrelin fragments and analogs thereof as well as to their therapeutic uses.

BACKGROUND

Ghrelin is a peptide which was isolated from the stomach but is expressed also in many other tissues, including the endocrine pancreas. It was discovered as a natural ligand of the growth-hormone secretagogue receptor type 1a (GHS-R) (Refs. 1, 2). Ghrelin acylation at serine 3 is essential for binding to GHS-R1a, which mediates GH-releasing activity and also the orexigenic action of acylated ghrelin. Besides stimulating GH secretion and modulating other pituitary functions, acylated ghrelin (AG) exerts a broad range of biological actions such as central regulation of food intake and energy balance and control of insulin secretion and glucose metabolism. GHS-R1a expression has been detected in a variety of endocrine and non-endocrine, central and peripheral animal and human tissues, including the pancreas. Notably, the link between ghrelin and insulin seems of major relevance. AG has been shown to possess hyperglycemic diabetogenic effects; ghrelin knock-out mice display enhanced glucose-induced insulin release while blockade of pancreatic islet-derived ghrelin has been shown to enhance insulin secretion and to prevent high-fat diet-induced glucose intolerance in rats.

In the endocrine pancreas, ghrelin has been shown to localize to α- and β-cells and to the newly identified ghrelin-producing islet ε-cells, suggesting a role in the regulation of β-cell fate and function (Refs. 9, 22, 19). Survival of β-cells is of major importance for maintaining normal glucose metabolism and β-cell apoptosis is a critical event in both type 1 and 2 diabetes (Refs. 16, 21).

Studies with several analogs of ghrelin with various aliphatic or aromatic groups in the side chain of residues 3 and several short peptides derived from ghrelin with various aliphatic or aromatic groups in the side chain of residue 3 and several short peptides derived from ghrelin as well showed that bulky hydrophobic groups in the side chain are essential for maximum agonist activity. In addition, short peptides encompassing the first four or five residues of ghrelin were found to functionally activate GHS-R 1a about as efficiently as the full-length ghrelin. Thus, the entire sequence of ghrelin is not necessary for activity; the Gly-Ser-Ser(n-octanoyl)-Phe [SEQ ID NO: 29] segment appears to constitute the active core required for agonist potency at GHS-R 1a." (Ref 2)

Unacylated ghrelin (UAG) is the major circulating form of ghrelin and has long been believed to be biologically inactive since it does not bind GHS-R1a at physiological concentrations and is thus devoid of GH-releasing activity. It is now known that UAG is a biologically active peptide, particularly at the metabolic level, having notably been shown to exert anti-diabetogenic effects as described in U.S. patent application Ser. No. 10/499,376, published on Apr. 14, 2005, under publication number US 2005-0080007. Indeed UAG is able to: a) counteract the hyperglycemic effect of AG in humans (Ref. 6); b) directly modulate glucose metabolism at the hepatic level by blocking basal, glucagon-induced and acylated ghrelin-stimulated glucose output from hepatocytes (Ref. 3); c) decrease fat deposition, food consumption, and glucose levels in UAG transgenic animals (Ref. 7); d) stimulate proliferation and prevent cell death and apoptosis in β-cells and human pancreatic islets (Ref. 4).

It has recently been demonstrated that UAG is able to stimulate proliferation and to prevent cell death and apoptosis induced by (IFN)-γ/tumor necrosis (TNF)-α, synergism in β-cells and human pancreatic islets (Ref. 4). Noteworthy, cytokine synergism is considered to be a major cause for β-cell destruction in type I diabetes as well as of β-cell loss in type 2 diabetes. Moreover, this work also showed that UAG stimulated glucose-induced insulin secretion from β-cells that do not express GHS-R1a.

Together, these results reinforce the concept that UAG has a therapeutic potential in medical conditions associated with metabolic disorder such as conditions characterized by insulin deficiencies or by insulin resistance, including, but not limited to diabetes, and the effect of UAG on the β-cells is one of the mechanisms of action of UAG in these potential applications.

Recently, the therapeutic potential of UAG was clinically demonstrated, as a continuous infusion of UAG in healthy volunteers resulted in a lowering of blood glucose, an improvement in insulin sensitivity, a reduction in blood free fatty acids, and decreased cortisol levels.

UAG is a 28 amino-acid peptide and would preferably be administered to patients by intravenous or subcutaneous injection in order to produce its effects, which is not a convenient way to administer a drug to a patient. Also, peptides of this size are usually rapidly degraded following administration and their in vivo efficacy is often weak following intravenous, subcutaneous or intramuscular bolus administration.

In addition, manufacturing a 28 amino-acid peptide is a long and expensive process, whether it is manufactured by solid-phase peptide synthesis or by recombinant technology. Finally, chronically treating patients with a long peptide such as UAG might represent safety risks for the patients in the form of immunogenicity. Raising neutralizing antibodies against a natural peptide is a potential major health risk for the patients.

Therefore, it would be highly desirable to identify smaller size peptides that would possess a comparable biological activity to UAG, but would be easier and less costly to manufacture.

It would be even more desirable that these smaller size peptides would have increased biological potency when compared with UAG.

Another advantage of these smaller size peptides would be that they would bear fewer immunogenicity risks for patients upon chronic and repeated administrations, and hence exhibit a better safety profile. They may have a better bioavailability than UAG, whatever the route of administration, and be suitable for more convenient routes of administration, such as, but not limited to, transdermal, pulmonary, intranasal or oral delivery, or may constitute a starting material for the design of peptide analogs or peptidomimetic molecules with a better oral bioavailability. Smaller size peptides may also be compatible with drug delivery system such as, but not limited to, polymer-based depot formulations.

SUMMARY

In one aspect of the present invention, there is provided an isolated polypeptide comprising any amino acid fragment of the amino acid sequence shown in SEQ ID NO: 9 or an analog thereof, wherein said polypeptide has at least one activity selected from the group consisting of a) decreasing blood glucose levels; b) increasing insulin secretion and/or sensitivity; c) binding to insulin-secreting cells; and d) promoting survival of insulin-secreting cells.

In one aspect of the present invention, there is provided an isolated polypeptide 5 to 27 amino acid residues in length, said polypeptide comprising the amino acid sequence Glu-His-Gln-Arg-Val.

In another aspect of the present invention, there is provided a method for treating a disorder associated with impaired glucose metabolism in a patient, comprising administering to the patient a therapeutically effective amount of the polypeptide as defined herein.

In another aspect of the present invention, there is provided a method for enhancing survival and/or proliferation of insulin-secreting cells comprising culturing said cells in the presence of a therapeutically effective amount of the polypeptide as defined herein.

In another aspect of the present invention, there is provided use of a therapeutically effective amount of the polypeptide as defined herein, in the preparation of a medicament for treating a disorder associated with impaired glucose metabolism in a patient.

In a further aspect of the present invention, there is provided use of a therapeutically effective amount of the polypeptide as defined herein, for treating a disorder associated with impaired glucose metabolism in a patient.

In a further aspect of the present invention, there is provided a pharmaceutical composition for treating a metabolic disorder associated with impaired glucose metabolism comprising a therapeutically effective amount of the polypeptide as defined herein.

In yet a further aspect of the present invention, there is provided an isolated polypeptide selected from the group consisting of SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 21, SEQ ID NO: 22, SEQ ID NO: 23, SEQ ID NO: 24, SEQ ID NO: 25, SEQ ID NO: 26, SEQ ID NO: 27 and SEQ ID NO: 28.

BRIEF DESCRIPTION OF THE FIGURES

FIG. 14A illustrates fed plasma glucose levels and FIG. 14B illustrates fasting plasma glucose.

DETAILED DESCRIPTION

Figure 1:
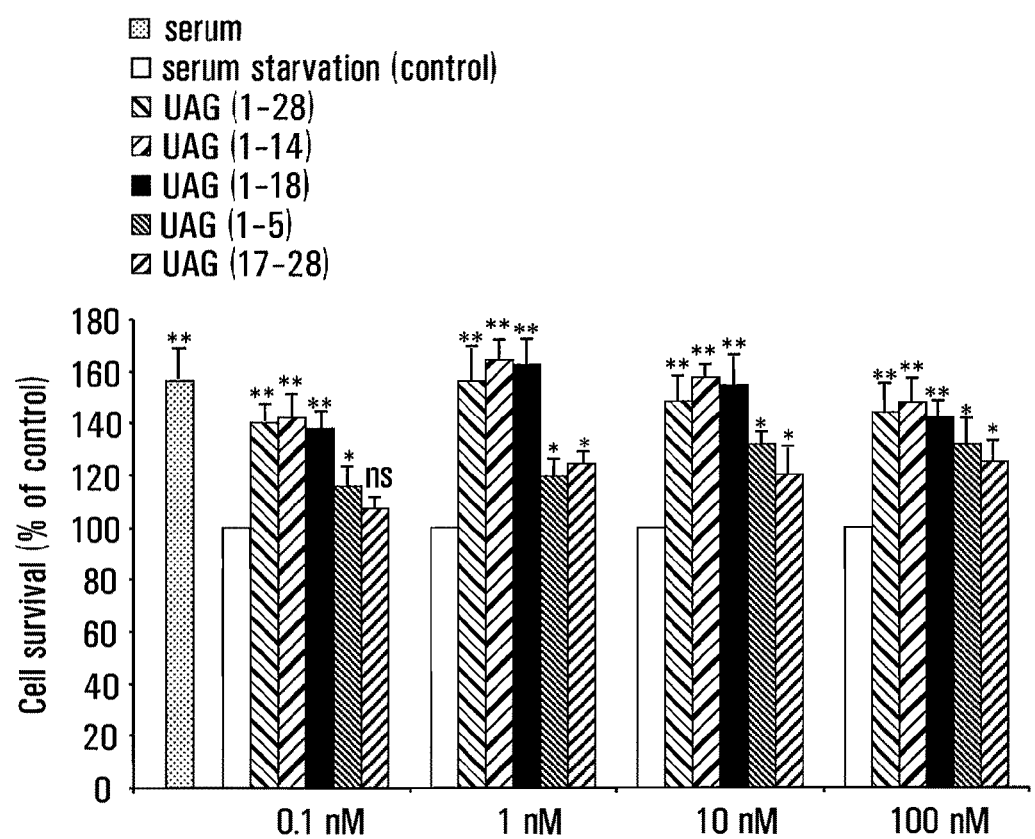
FIG. 1 illustrates survival of INS-1E β-cells in serum-free medium in the presence of unacylated ghrelin or the indicated fragments of unacylated ghrelin.

Unless defined otherwise, all technical and scientific terms used herein have the same meaning as commonly understood by one of skill in the art to which the invention belongs.

UAG Fragments and Analogs Thereof.

For the purpose of the present invention the following terms are defined below.

In the present application, the terms "ghrelin" and "acylated ghrelin" or "AG" are used interchangeably and have the same meaning.

The term "unacylated ghrelin" or "UAG" is intended to mean peptides that contain the amino acid sequence specified in SEQ ID NO: 1 (1-NH₂Gly-Ser-Ser-Phe-Leu-Ser-Pro-Glu-His-Gln-Arg-Val-Gln-Gln-Arg-Lys-Glu-Ser-Lys-Lys-Pro-Pro-Ala-Lys-Leu-Gln-Pro-Arg-28; SEQ ID NO: 1). UAG may also be referred to as UAG (1-28).

Naturally-occurring variations of unacylated ghrelin include peptides that contain substitutions, additions or deletions of one or more amino acids which result due to discrete changes in the nucleotide sequence of the encoding ghrelin gene or alleles thereof or due to alternative splicing of the transcribed RNA. It is understood that the said changes do not substantially affect the properties, pharmacological and biological characteristics of unacylated ghrelin variants. Those peptides may be in the form of salts. Particularly the acidic functions of the molecule may be replaced by a salt derivative thereof such as, but not limited to, a trifluoroacetate salt.

As used herein, SEQ ID NO: 9 refers to the amino acid sequence consisting of residues 6 to 18 of UAG (SEQ ID NO: 1), namely: 6-Ser-Pro-Glu-His-Gln-Arg-Val-Gln-Gln-Arg-Lys-Glu-Ser-18.

By "peptide", "polypeptide" or "protein" is meant any chain of amino acids, regardless of length or post-translational modification (e.g., glycosylation or phosphorylation), or chemical modification, or those containing unnatural or unusual amino acids such as D-Tyr, ornithine, amino-adipic acid. The terms are used interchangeably in the present application.

The term "fragments" or "fragments thereof" refers to amino acid fragments of a peptide such as unacylated ghrelin. Fragments of unacylated ghrelin are shorter than 28 amino acid residues. Fragments of unacylated ghrelin may therefore be 27, 26, 25, 24, 23, 22, 21, 20, 19, 18, 17, 16, 15, 14, 13, 12, 11, 10, 9, 8, 7, 6, 5 or 4 amino acid residues in length.

In some aspects of the invention, the polypeptides are used in a form that is "purified", "isolated" or "substantially pure" The polypeptides are "purified", "isolated" or "substantially pure" when they are separated from the components that naturally accompany them. Typically, a compound is substantially pure when it is at least 60%, 65%, 70%, 75%, 80%, 85%, 90%, 95%, 96%, 97%, 98%, or 99%, by weight, of the total material in a sample.

The term "analog of unacylated ghrelin", "analog of fragments of unacylated ghrelin" or "analogs thereof" refers to both structural and functional analogs of unacylated ghrelin or fragments thereof which are, inter alia, capable of replacing unacylated ghrelin in antagonizing the peripheral actions or functions of ghrelin or are capable of replacing other biological actions of unacylated ghrelin, such as, but not limited to, stimulate proliferation and/or inhibit apoptosis in β-cell lines, lower blood glucose levels, improved insulin sensitivity and/or secretion, decrease cortisol levels, improve lipid profile in human beings, and thus, have the potential use to treat metabolic disorders such as those associated with for example, insulin resistance, insulin deficiency, dyslipidemia or cortisol excess.

Simple structural analogs comprise peptides showing homology with unacylated ghrelin as set forth in SEQ ID NO: 1 or homology with any fragments thereof. For example, an isoform of ghrelin-28 (SEQ ID NO: 1), des Gln-14 Ghrelin (a 27 amino acid peptide possessing serine 3 modification by n-octanoic acid) is shown to be present in stomach. It is functionally identical to ghrelin in that it binds to GHSR-1a with similar binding affinity, elicits $Ca^{2+}$ fluxes in cloned cells and induces GH secretion with similar potency as Ghrelin-28. It is expected that UAG also has a des Gln-14 UAG that is functionally identical to UAG.

Preferred analogs of UAG and preferred analogs of fragments of UAG are those that vary from the native UAG sequence or from the native UAG fragment sequence by conservative amino acid substitutions; i.e., those that substitute a residue with another of like characteristics. Typical substitutions include those among Ala, Val, Leu and Ile; among Ser and Thr; among the acidic residues Asp and Glu; among Asn and Gln; among the basic residues Lys and Arg; and among the aromatic residues Phe and Tyr. Particularly preferred are analogs in which several, for example, but not limited to, 5-10, 1-5, or 1-2 amino acids are substituted, deleted, or added in any combination. For example, the analogs of UAG may differ in sequence from UAG by 1, 2, 3, 4, 5, 6, 7, 8, 9 or 10 amino acid substitutions (preferably conservative substitutions), deletions, or additions, or combinations thereof.

There are provided herein, analogs of the peptides of the invention that have at least 50%, 55%, 60%, 65%, 70%, 75%, 80%, 85%, 90%, 95%, 96%, 97%, 98% or 99% sequence homology with the amino acid sequences described herein over its full length, and sharing at least one of the metabolic effects or biological activity of UAG. A person skilled in the art would readily identify an analog sequence of unacylated ghrelin or an analog sequence of a fragment of unacylated ghrelin.

In a further aspect, analogs of UAG or fragments thereof are, for example, analogs obtained by alanine scans, by substitution with D-amino acids or with synthetic amino acids or by cyclization of the peptide. Analogs of UAG or fragments thereof may comprise a non-naturally encoded amino acid, wherein the non-naturally encoding amino acid refers to an amino acid that is not one of the common amino acids or pyrrolysine or selenocysteine, or an amino acid that occur by modification (e.g. post-translational modification) of naturally encoded amino acid (including, but not limited to, the 20 common amino acids or pyrrolysine and selenocysteine) but are not themselves incorporated into a growing polypeptide chain by the translation complex. Examples of such non-naturally-occurring amino acids include, but are not limited to, N-acetylglucosaminyl-L-serine, N-acetylglucosaminyl-L-threonine and O-phosphotyrosine.

As used herein, the term "modified" refers to any changes made to a given polypeptide, such as changes to the length of the polypeptide, the amino acid sequence, chemical structure, co-translational modification, or post-translational modification of a polypeptide.

The term "post-translational modification" refers to any modification of a natural or non-natural amino acid that occurs to such an amino acid after it has been incorporated into a polypeptide chain. The term encompasses, by way of example only, co-translational in vivo modifications, co-translational in vitro modifications (such as in cell-free translation system), post-translational in vivo modifications, and post-translational in vitro modifications. Examples of post-translational modifications are, but are not limited to, glycosylation, acetylation, acylation, amidation, carboxylation, phosphorylation, addition of salts, amides or esters, in particular C-terminal esters, and N-acyl derivatives of the peptides of the invention. The types of post-translational modifications are well known.

Certain peptides according to the present invention may also be in cyclized form, such that the N- or C-termini are linked head-to-tail either directly, or through the insertion of a linker moiety, such moiety itself generally comprises one or more amino acid residues as required to join the backbone in such a manner as to avoid altering the three-dimensional structure of the peptide with respect to the non-cyclized form. Such peptide derivatives may have improved stability and bioavailability relative to the non-cyclized peptides. Methods for cyclizing peptides are well known in the art.

Cyclisation may be accomplished by disulfide bond formation between two side chain functional groups, amide or ester bond formation between one side chain functional group and the backbone α-amino or carboxyl function, amide or ester bond formation between two side chain functional groups, or amide bond formation between the backbone α-amino and carboxyl functions. These cyclisation reactions have been traditionally carried out at high dilution in solution. Cyclisation is commonly accomplished while the peptide is attached to the resin. One of the most common ways of synthesising cyclic peptides on a solid support is by attaching the side chain of an amino acid to the resin. Using appropriate protection strategies, the C- and N-termini can be selectively deprotected and cyclised on the resin after chain assembly. This strategy is widely used, and is compatible with either tert-butyloxycarbonyl (Boc) or 9-fluorenylmethoxycarbonyl (Fmoc) protocols. However, it is restricted to peptides that contain appropriate side chain functionality to attach to the solid support. A number of approaches may be used to achieve efficient synthesis of cyclic peptides. One procedure for synthesising cyclic peptides is based on cyclisation with simultaneous cleavage from the resin. After an appropriate peptide sequence is assembled by solid phase synthesis on the resin or a linear sequence is appended to resin, the deprotected amino group can react with its anchoring active linkage to produce protected cyclic peptides. In general, a final deprotection step is required to yield the target cyclic peptide. The procedure for synthesising cyclic peptides are well known in the art.

For example, lactamazation, a form of cyclisation, may be performed to form a lactam bridge using Fmoc synthesis, amino acids with different protecting groups at the lateral chains may be introduced, such as, but not limited to, aspartic acid (or glutamic) protected with allyl ester at the beta ester (or gamma ester for glutamic acid) and lysine protected with allyloxy carbamate at the N-ε. At the end of the synthesis, with the N-terminus of the peptide protected with Fmoc, Boc or other protecting group different from Alloc, the allyl and alloc protecting groups of aspartic acid and lysine may be deprotected with, for example, palladium (0) followed by cyclization using PyAOP (7-Azabenzotriazol-1-yloxytris (pyrrolidino) phosphonium-hexafluorophosphate) to produce the lactam bridge.

Unless otherwise indicated, an amino acid named herein refers to the L-form. Well recognised abbreviations in the art will be used to describe amino acids, including levoratory amino acids (L-amino acids or L or L-form) and dextrorotary amino acids (D-amino acids or D or D-form), Alanine (Ala or A), Arginine (Arg or R), Asparagine (Asn or N), Aspartic acid (Asp or D), Cysteine (Cys or C), Glutamic acid (Glu or E), Glutamine (Gln or Q), Glycine (Gly or G), Histidine (His or H), Isoleucine (Ile or I), Leucine (Leu or L), Lysine (Lys or K), Methionine (Met or M), Phenylalanine (Phe or F), Proline (Pro or P), Serine (Ser or S), Threonine (Thr or T), Tryptophan (Trp or W), Tyrosine (Tyr or Y) and Valine (Val or V). An L-amino acid residue within the native peptide sequence may be altered to any one of the 20 L-amino acids commonly found in proteins or any one of the corresponding D-amino acids, rare amino acids, such as, but not limited to, 4-hydroxyproline or hydroxylysine, or a non-protein amino acid, such as P-alanine or homoserine.

Any other analogs of UAG or fragments thereof or any other modified UAG or fragments thereof that preserve the biological activity of UAG are encompassed by the present invention.

General methods and synthetic strategies used in providing functional and structural analogs of UAG or fragments thereof are commonly used and well known in the art and are described in publications such as "Peptide synthesis protocols" ed, M. W. Pennigton & B. M. Dunn. Methods in Molecular Biology. Vol 35. Humana Press, NJ., 1994.

The term "homology" refers to sequence similarity between two peptides while retaining an equivalent biological activity. Homology can be determined by comparing each position in the aligned sequences. A degree of homology between amino acid sequences is a function of the number of identical or matching amino acids at positions shared by the sequences so that a "homologous sequence" refers to a sequence sharing homology and an equivalent function or biological activity. Assessment of percent homology is known by those of skill in the art.

Methods to determine identity and similarity of peptides are codified in publicly available computer programs. Preferred computer program methods to determine identity and similarity between two sequences include, but are not limited to, the GCG program package, BLASTP, BLASTN, and FASTA. The BLAST X program is publicly available from NCBI and other sources. The well known Smith Waterman algorithm may also be used to determine identity.

Preferred parameters for polypeptide sequence comparison include the following:
Algorithm: Needleman and Wunsch, J. MoI Biol. 48: 443-453 (1970);
Comparison matrix: BLOSSUM62 from Hentikoff and Hentikoff, Proc. Natl. Acad. Sci. USA. 89:10915-10919 (1992);
Gap Penalty: 12; Gap Length Penalty: 4.

A program useful with these parameters is publicly available as the "gap" program from Genetics Computer Group, Madison, Wis. The aforementioned parameters are the default parameters for amino acid sequence comparisons (along with no penalty for end gaps).

The polypeptides of the invention may be prepared in any suitable manner as known in the art. Such polypeptides include isolated naturally occurring polypeptides, recombinantly produced polypeptides, synthetically produced polypeptides, or polypeptides produced by a combination of these methods. Means and methods for preparing such polypeptides are well known in the art.

Certain aspects of the invention use UAG polynucleotides. These include isolated polynucleotides which encode the UAG polypeptides, fragments and analogs defined in the application.

As used herein, the term "polynucleotide" refers to a molecule comprised of a plurality of deoxyribonucleotides or nucleoside subunits. The linkage between the nucleoside subunits can be provided by phosphates, phosphonates, phosphoramidates, phosphorothioates, or the like, or by nonphosphate groups as are known in the art, such as peptoid-type linkages utilized in peptide nucleic acids (PNAs). The linking groups can be chiral or achiral. The oligonucleotides or polynucleotides can range in length from 2 nucleoside subunits to hundreds or thousands of nucleoside subunits. While oligonucleotides are preferably 5 to 100 subunits in length, and more preferably, 5 to 60 subunits in length, the length of polynucleotides can be much greater (e.g., up to 100). The polynucleotide may be any of DNA and RNA. The DNA may be in any form of genomic DNA, a genomic DNA library, cDNA derived from a cell or tissue, and synthetic DNA. Moreover, the present invention may, in certain aspects, use vectors which include bacteriophage, plasmid, cosmid, or phagemid.

Survival Effect of UAG Fragments and Analogs Thereof.

In one aspect of the invention, the proliferative and anti-apoptotic effects of UAG fragments and analogs thereof vs. UAG in INS-1E β-cell line, HIT-T15 β-cell line as well as in human pancreatic islets were investigated.

UAG fragments and analogs thereof which stimulate proliferation and/or inhibit apoptosis in these cell lines will also bear other metabolic properties of UAG including, but not limited to, lowering blood glucose levels, improving insulin sensitivity, decreasing cortisol levels, improving lipid profile in human beings, and thus, have the potential use to treat metabolic disorders associated, for example, with insulin resistance, insulin deficiency, dyslipidemia or cortisol excess.

In one aspect of the invention, the survival effects of some human UAG fragments listed in Table 1 below were analyzed:

TABLE 1

| NAME | SEQ ID NO: | SEQUENCE |
|---|---|---|
| UAG (1-14) | 2 | Gly-Ser-Ser-Phe-Leu-Ser-Pro-Glu-His-Gln-Arg-Val-Gln-Gln |
| UAG (1-18) | 3 | Gly-Ser-Ser-Phe-Leu-Ser-Pro-Glu-His-Gln-Arg-Val-Gln-Gln-Arg-Lys-Glu-Ser |
| UAG (1-5) | 4 | Gly-Ser-Ser-Phe-Leu |
| UAG (17-28) | 5 | Glu-Ser-Lys-Lys-Pro-Pro-Ala-Lys-Leu-Gln-Pro-Arg |
| UAG (6-13) | 6 | Ser-Pro-Glu-His-Gln-Arg-Val-Gln |
| UAG (8-13) | 7 | Glu-His-Gln-Arg-Val-Gln |
| UAG (8-12) | 8 | Glu-His-Gln-Arg-Val |
| UAG (8-11) | 10 | Glu-His-Gln-Arg |
| UAG (9-12) | 11 | His-Gln-Arg-Val |
| UAG (9-11) | — | His-Gln-Arg |

The UAG fragments listed in Table 2 below were also analysed:

TABLE 2

| NAME | SEQ ID NO: | SEQUENCE (amino acid residues 6 to 13 of SEQ ID NO: 1) |
|---|---|---|
| (Asp)8 UAG (6-13)NH$_2$ | 12 | Ser-Pro-Asp-His-Gln-Arg-Val-Gln-NH$_2$ |
| (Lys)11 UAG (6-13)NH$_2$ | 13 | Ser-Pro-Glu-His-Gln-Lys-Val-Gln-NH$_2$ |
| (Gly)6 UAG (6-13)NH$_2$ | 14 | Gly-Pro-Glu-His-Gln-Arg-Val-Gln-NH$_2$ |
| (Ala)6 UAG (6-13)NH$_2$ | 15 | Ala-Pro-Glu-His-Gln-Arg-Val-Gln-NH$_2$ |
| (Ala)7 UAG (6-13)NH$_2$ | 16 | Ser-Ala-Glu-His-Gln-Arg-Val-Gln-NH$_2$ |
| (Ala)8 UAG (6-13)NH$_2$ | 17 | Ser-Pro-Ala-His-Gln-Arg-Val-Gln-NH$_2$ |
| (Ala)9 UAG (6-13)NH$_2$ | 18 | Ser-Pro-Glu-Ala-Gln-Arg-Val-Gln-NH$_2$ |
| (Ala)10 UAG (6-13)NH$_2$ | 19 | Ser-Pro-Glu-His-Ala-Arg-Val-Gln-NH$_2$ |
| (Ala)11 UAG (6-13)NH$_2$ | 20 | Ser-Pro-Glu-His-Gln-Ala-Val-Gln-NH$_2$ |
| (Ala)12 UAG (6-13)NH$_2$ | 21 | Ser-Pro-Glu-His-Gln-Arg-Ala-Gln-NH$_2$ |
| (Ala)13 UAG (6-13)NH$_2$ | 22 | Ser-Pro-Glu-His-Gln-Gln-Arg-Val-Gln-NH$_2$ |
| (Acetyl-Ser)6 UAG (6-13)NH$_2$ | 23 | Ac-Ser-Pro-Glu-His-Gln-Arg-Val-Gln-NH$_2$ |
| (Acetyl-Ser)6, (DPro)7 UAG(6-13)NH$_2$ | 24 | Ac-Ser-pro-Glu-His-Gln-Arg-Val-Gln-NH$_2$ |
| Cyclo (6-13) UAG | 25 | Ser-Pro-Glu-His-Gln-Arg-Val-Gln (cycl) |
| Cyclo (8, 11), Lys 11, UAG(6-13) amide | 26 | Ser-Pro-Glu-His-Gln-Lys-Val-Gln-amide |
| Cyclo (8, 11), Acetyl-Ser6, Lys 11, UAG (6-13)-amide | 27 | Ac-Ser-Pro-Glu-His-Gln-Lys-Val-Gln (cycl) |
| Acetyl-Ser6, Lys 11, UAG(6-13)NH$_2$ | 28 | Ac-Ser-Pro-Glu-His-Gln-Lys-Val-Gln-NH$_2$ |

Figure 2:
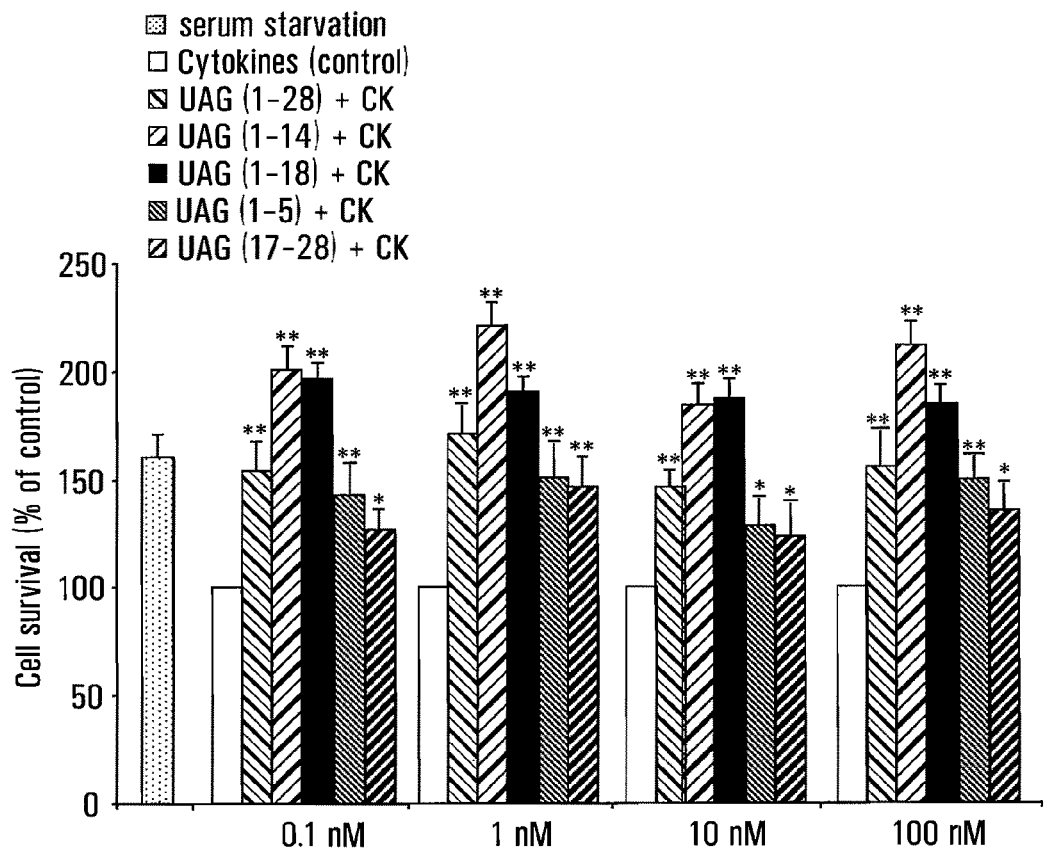
FIG. 2 illustrates survival of INS-1E β-cells in the presence of TNF-α/IFN-γ/IL-1β and in the presence of unacylated ghrelin or the indicated fragments of unacylated ghrelin.
Figure 3A:
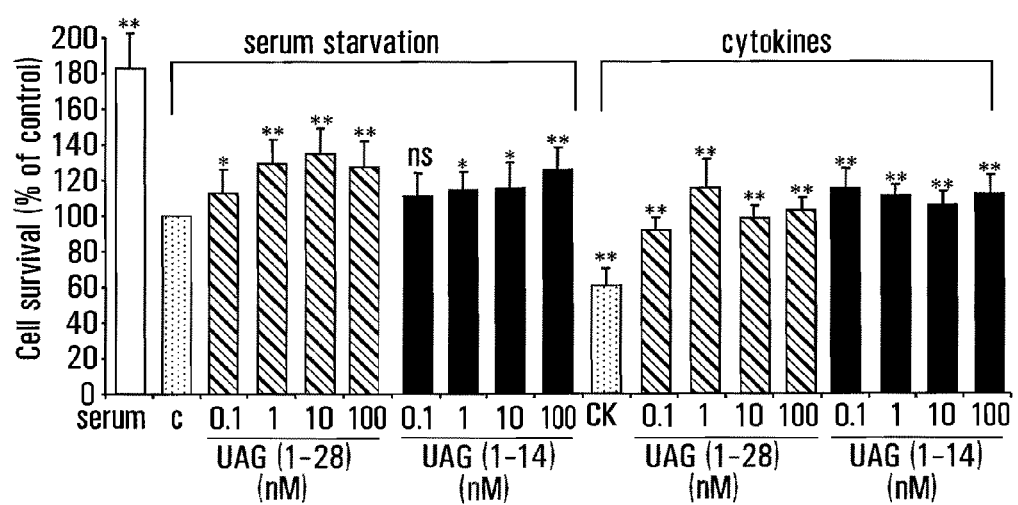
FIGS. 3A and 3B illustrate survival of HIT-T15 β-cells in serum free medium with or without cytokines and either unacylated ghrelin UAG (1-28) or its fragment UAG (1-14) (FIG. 3A) or UAG (1-18) (FIG. 3B).
Figure 3B:
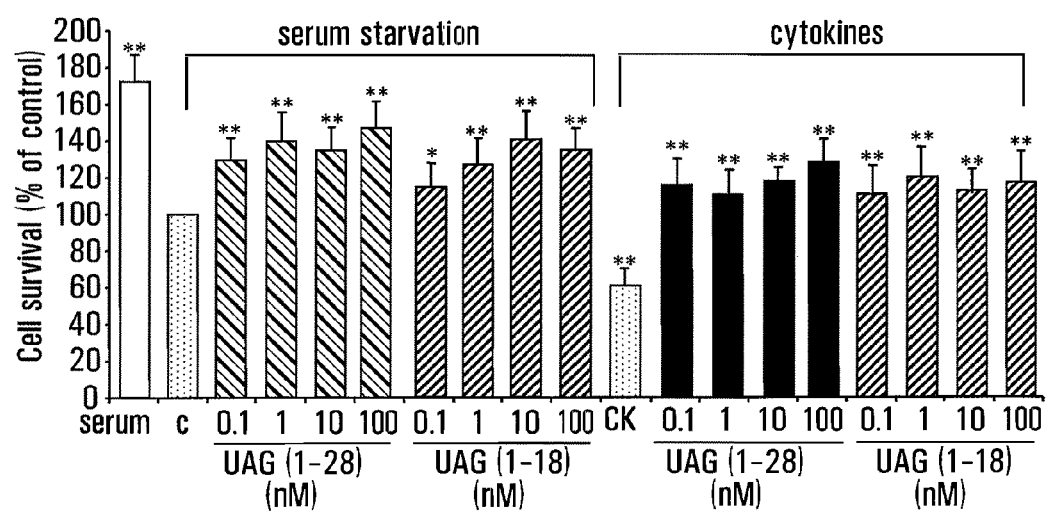
Figure 4A:
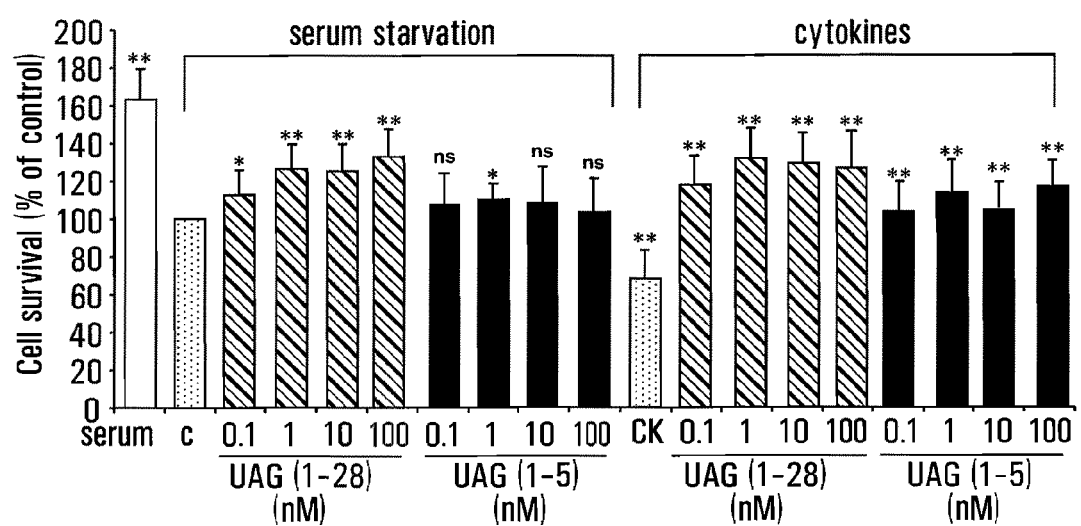
FIGS. 4A and 4B illustrate survival of HIT-T15 β-cells in serum free medium with or without cytokines and either unacylated ghrelin UAG (1-28) or its fragments UAG (1-5) (FIG. 4A) or UAG (17-28) (FIG. 4B).
Figure 4B:
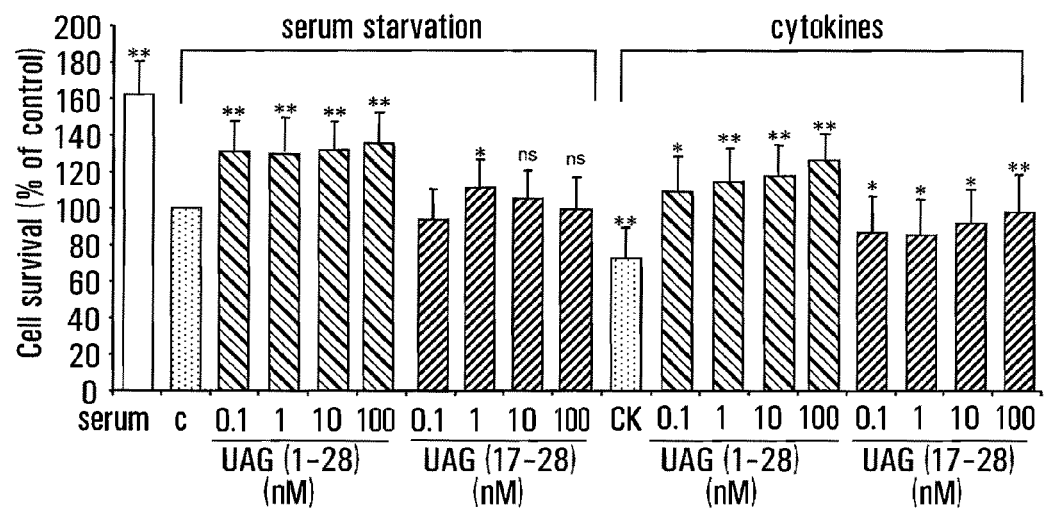
Figure 5A:
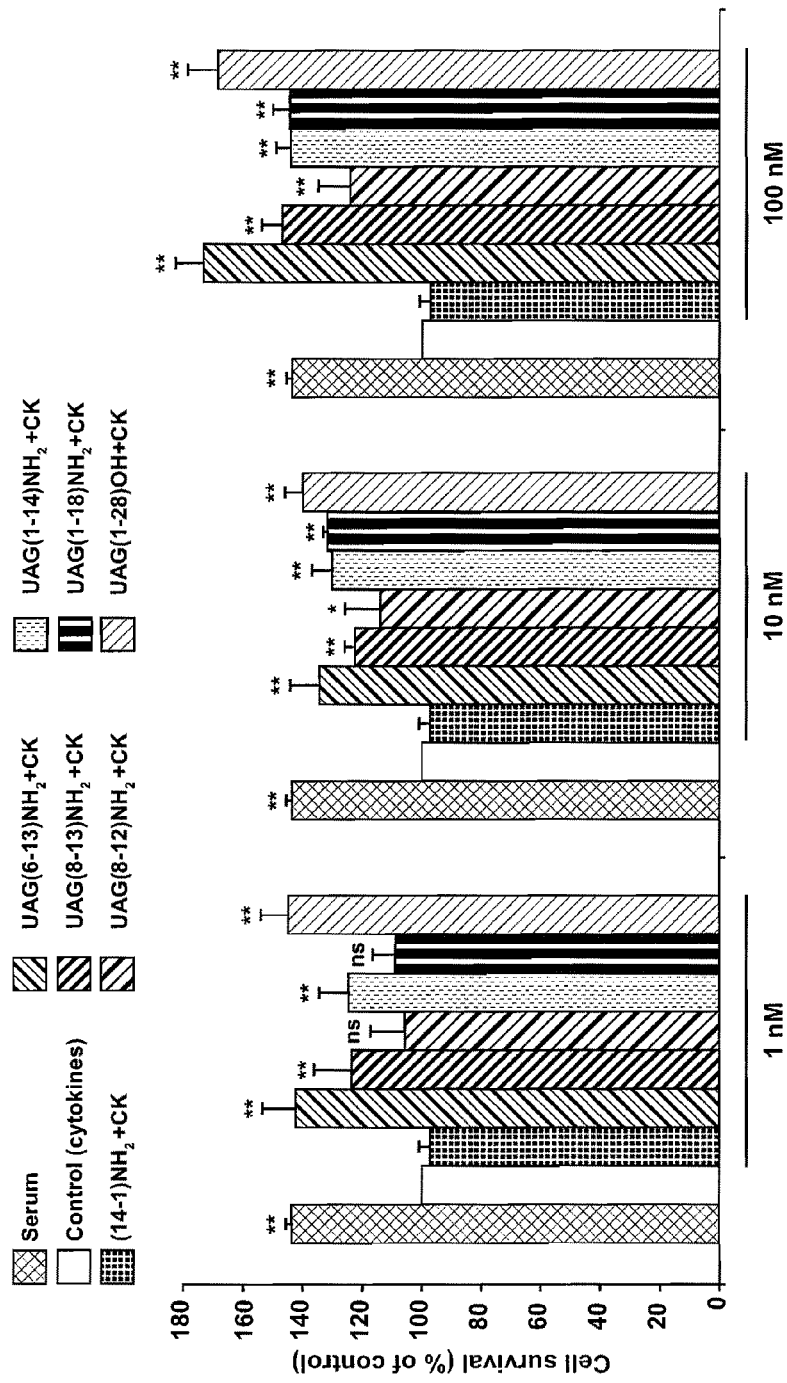
FIGS. 5A and 5B illustrate survival of cytokine-treated HIT-T15 β-cell in the presence of unacylated ghrelin fragments UAG (6-13), UAG (8-13), UAG (8-12), UAG (1-14), UAG (1-18), UAG (1-28) (FIG. 5A) and UAG (8-11), UAG (9-12) and UAG (9-11) (FIG. 5B).

UAG (1-14) and UAG (1-18) potently increased cell survival of both INS-1E β-cells and HIT-T15 β-cells in either serum-free conditions and after treatment with cytokines (FIGS. 1-2 for INS-1E cells, FIGS. 3A, 3B, 4A and 4B for HIT-T15 β-cells). These effects were similar to that displayed by the full-length molecule UAG (1-28). UAG (1-14) appeared even stronger than native UAG as a protection against cytokine-induced apoptosis in INS-1E cells. UAG (1-5) and UAG (17-28) exerted only a trivial effect in INS-1E cells (FIGS. 1-2) and very little effect in HIT-T15 cells (FIGS. 4A and 4B). Surprisingly, the short fragments UAG (6-13), UAG (8-13) and UAG (8-12) were all strongly effective in increasing survival in cytokine-induced apoptosis in HIT-T15 cells (FIG. 5A). Actually, peptides UAG (8-12) and UAG (8-13) were at least as potent as UAG (1-14), whereas peptide UAG (6-13) was clearly superior. UAG (1-5) and UAG (17-28) were only minimally effective.

Figure 6A:
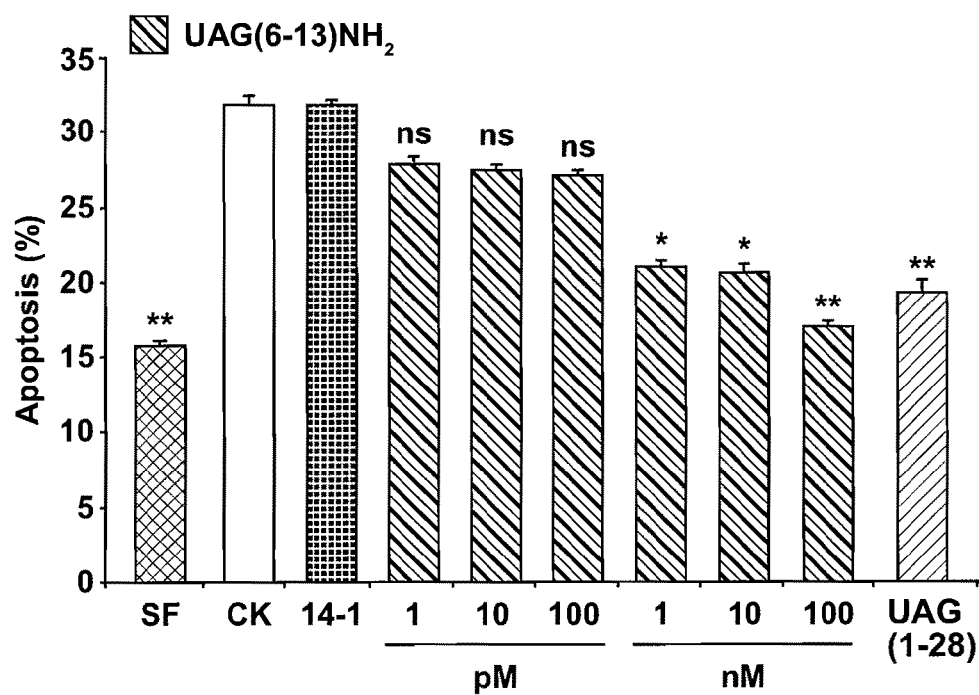
FIGS. 6A to 6C illustrate the antiapoptotic effects of unacylated ghrelin fragments UAG (6-13) (FIG. 6A), UAG (8-13) (FIG. 6B) and UAG (8-12) (FIG. 6C) on cytokine treated HIT-T15 β-cells
Figure 6B:
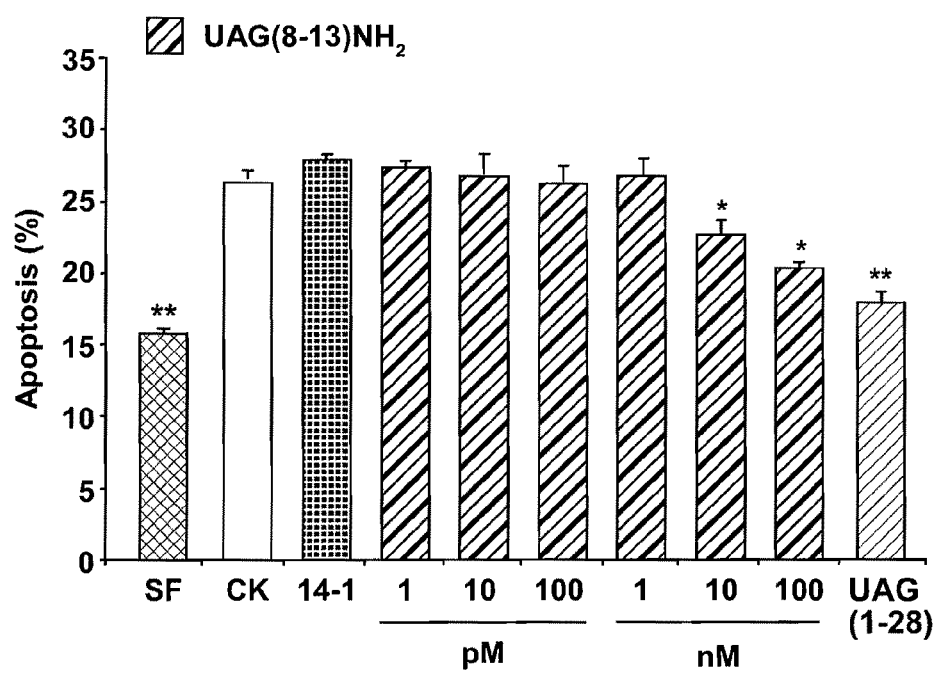
Figure 6C:
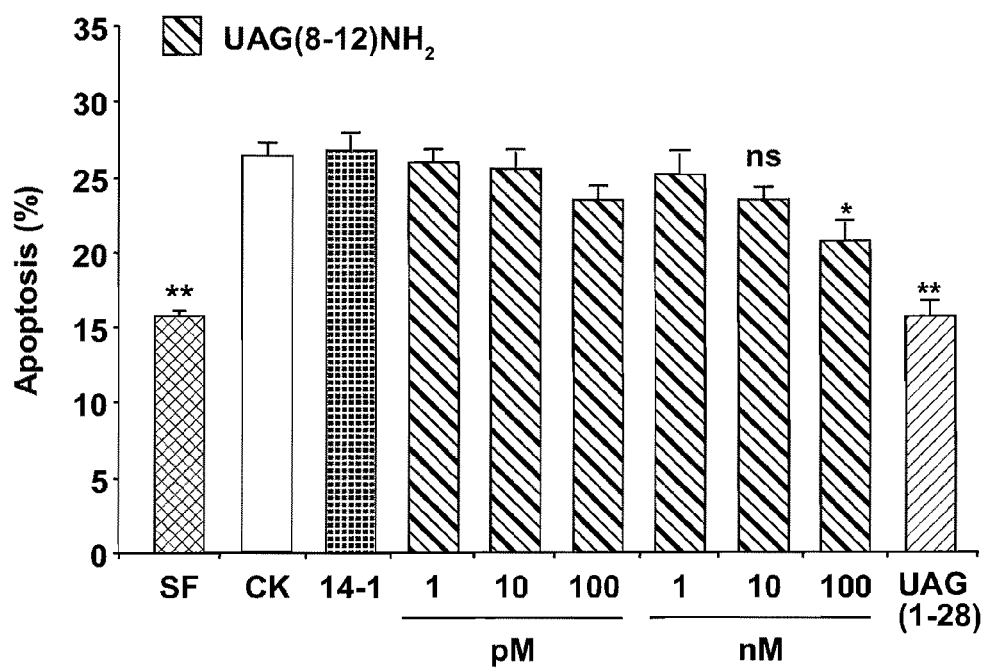

UAG (6-13), UAG (8-12) and UAG (8-13) were shown to exert the strongest antiapoptotic effect in HIT-T15 β-cells treated with cytokines (FIGS. 6A, 6B and 6C).

The data presented herein demonstrate that UAG fragments potently increase cell survival and prevent cell death in β-cell lines with potencies very comparable to that of the full-length UAG itself or better. UAG (1-14) exhibited a potency equivalent to, if not better than full-length UAG itself, whereas the (8-12) fragment, a 5 amino-acid peptide, retained all the biological activity and UAG (6-13) was even more potent.

Figure 7A:
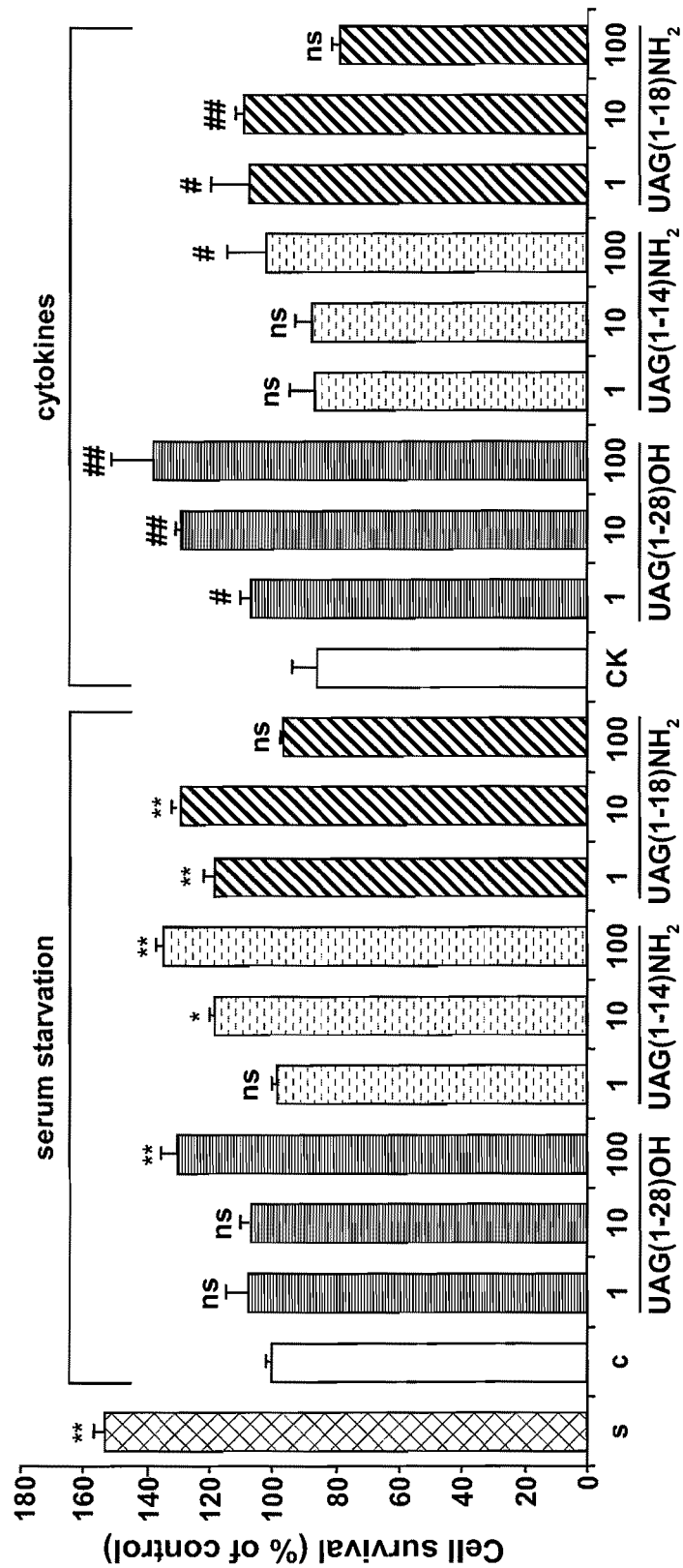
FIGS. 7A and 7B illustrate the survival effect on human pancreatic islets of unacylated ghrelin (1-28) and its fragments UAG (1-14), UAG (1-18) (FIG. 7A) and UAG (1-5) and UAG (17-28) (FIG. 7B).
Figure 7B:
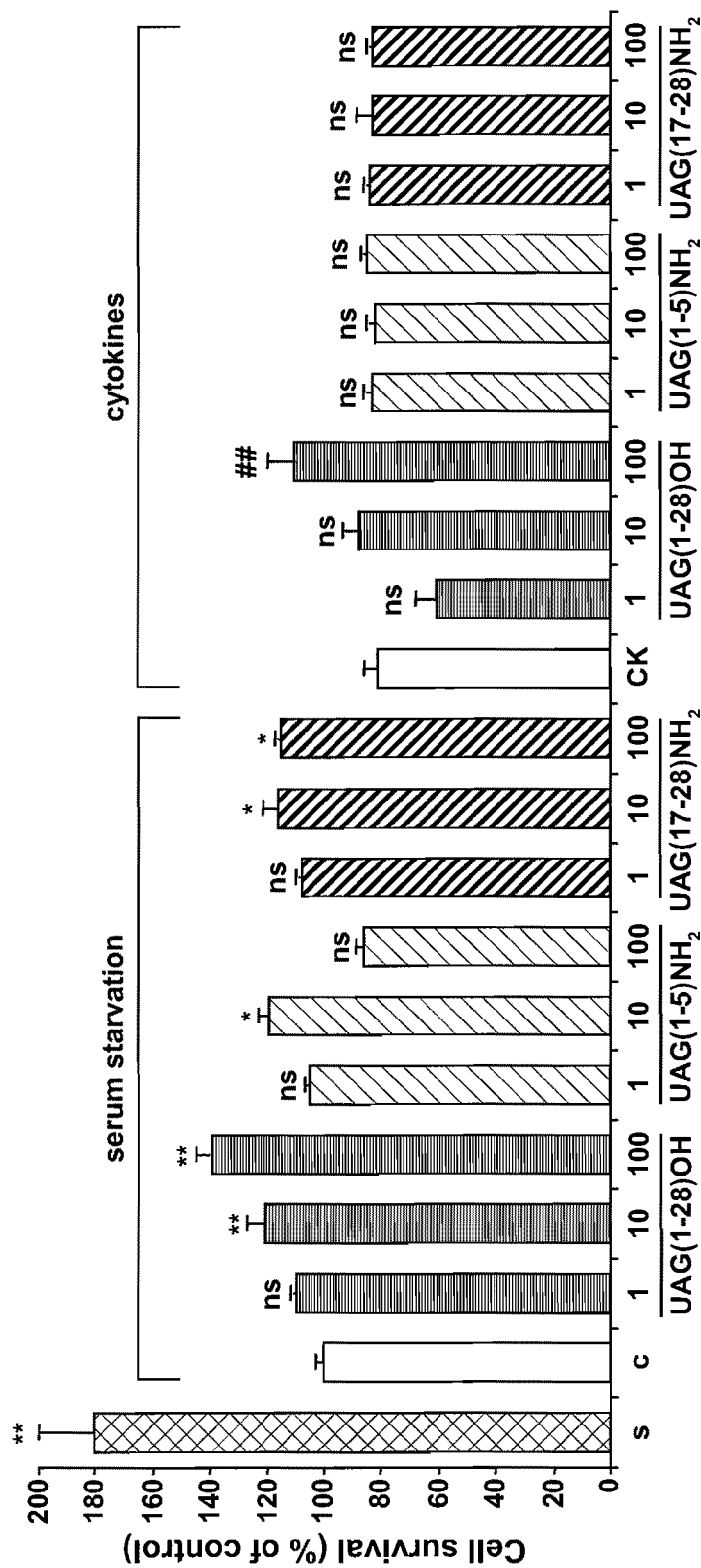

In another aspect of the invention, the data presented herein also demonstrate the survival effect of UAG fragments in human pancreatic islets (FIGS. 7A and 7B). UAG (1-14) and UAG (1-18) exert protective effects in serum-free conditions that are similar to those displayed by UAG (1-28). On the other hand, the protective effect of UAG (1-5) and (17-28) in human islets is reduced or even absent in the experimental conditions tested.

Effect of UAG Fragments or Analogs Thereof on Insulin Secretion

The effects of UAG (1-14) and UAG (1-18) on insulin secretion in human islets was also investigated. UAG (1-14), similarly to UAG (1-28), and to exendin-4, significantly increased glucose-induced insulin secretion in both HIT-T15 β-cells (data not shown) and in human islets (FIGS. 8A to 8D).

UAG Fragment and Analogs Thereof Reduce Diabetes In Vivo

Figure 9A:
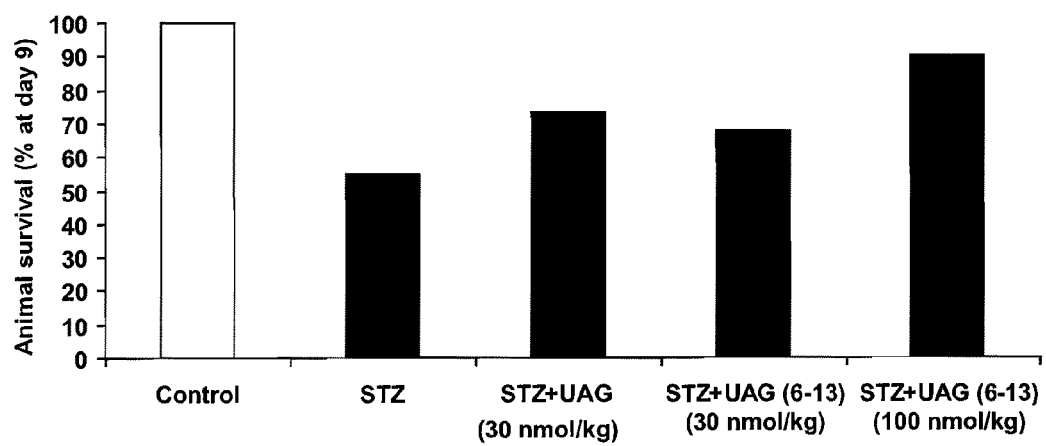
FIGS. 9A to 9D illustrate the in vivo effect of unacylated ghrelin fragment UAG (6-13) on animal survival (FIG. 9A), on plasma glucose levels (FIG. 9B) and plasma (FIG. 9C) and pancreatic (FIG. 9D) insulin levels, in Streptozotocin (STZ)-treated animals.

In a further aspect, the data presented herein also show that UAG fragments, for example UAG (6-13), increase survival of Streptozotocin (STZ)-treated animals (FIG. 9A). UAG fragments also reduce STZ-induced plasma glucose (FIG. 9B) and improve both plasma and pancreatic insulin levels (FIGS. 9C and 9D) in STZ-induced diabetic rats. The data presented herein also demonstrate that UAG fragments, for example UAG (6-13), suppress plasma glucose levels, enhance insulin sensitivity and modulate diabetes in vivo (FIGS. 14A, 14B and 15) and reduces body fat weight (FIG. 16).

Binding of UAG Fragments and Analogs Thereof to β-Cells

In a further aspect, the data presented herein demonstrate that UAG (6-13), UAG (1-14) and UAG (1-13) recognized and bound to the UAG receptor on HIT-T15 and INS-1E pancreatic β-cells. Among these, UAG (6-13) displayed the highest binding activity and possessed a binding affinity very close to that of the naturally occurring UAG. This finding, in conjunction with the functional in vitro studies showing that UAG (6-13) exerts, similarly to native UAG, prosurvival effects on HIT-T15 cells, indicate that UAG (6-13) is a potent UAG agonist with potential anti-diabetic activity.

Thus it appears that the active sequence of UAG to obtain its metabolic effects resides in the region containing residues 8-12. This observation clearly differentiates the structure-activity relationship of UAG to that of acylated ghrelin, for which the minimally active sequence is ghrelin (1-5), the serine residue in position 3 being octanoylated. This further reinforces the hypothesis that UAG exerts its metabolic effects through one or several receptors other than GHS-R1a, the receptor mediating the effects of acylated ghrelin on growth hormone secretion.

Therefore, and very surprisingly, these results show that the full-length UAG sequence is not necessary for UAG to produce its biological effects on β-cells and on human islet. UAG (1-14) and UAG (1-18) are at least as potent as native UAG. Even more surprisingly, UAG (8-12) and UAG (8-13) retained all the biological activity of full-length UAG, and UAG (6-13) was even more potent than UAG (1-14).

The results indicate that UAG (8-12) or any peptide comprising this 5 amino acid sequence, whether amidated or not, or any peptide comprising, for example, any analogs of UAG (6-13), UAG (8-12) or UAG (8-13) will share the same metabolic or biological effects as UAG itself. Any peptide comprising a fragment of at least 5, or at least 6, or at least 7, or at least 8 amino acid residues of the amino acid sequence containing residues 6 to 18 of UAG and including at least the amino acid sequence UAG (8-12) are also preferred.

In a further aspect, the present invention provides for peptides comprising UAG (8-12) or UAG (8-13) or UAG (6-13) or any analogs thereof having the property to stimulate the proliferation β-cells, to improve survival and/or inhibit death of β-cells, to decrease plasma glucose level, to increase insulin secretion and/or sensitivity, to decrease blood lipids, such as free fatty acids and triglycerides, to reduce cortisol secretion, to bind to β-cells, which make them useful, for example, for the treatment of disorders associated with impaired glucose metabolism, impaired insulin metabolism, type I diabetes, type II diabetes and/or to improve the engraftment of pancreatic islets, whether by ex vivo treatment of the graft or by administration in the patient. The peptides are also useful to treat medical conditions associated in insulin resistance, insulin deficiency, lower blood glucose, useful for the treatment of diabetes, obesity and dyslipidemia. Assays for measuring the properties of the polypeptides of the invention and the procedures for carrying out these assays are well known in the art.

In a further aspect, the present invention provides for analogs of UAG fragments which retain the biological activity of UAG. Examples of such analogs are, but are not limited to, (Asp)8 UAG (6-13) where E (Glu) is substituted by D (Asp), which is as active as UAG (6-13). The activity of this analog illustrates that a substitution of an acidic amino-acid by another acidic residue preserves the biological activity of UAG (6-13). (Lys)11 UAG (6-13) where R (Arg) is substituted by K (Lys), is also as active as UAG (6-13), illustrating the fact that a substitution of a basic amino-acid by another basic residue preserves the biological activity of UAG (6-13). (Gly)6 UAG (6-13) where S (Ser) is substituted by G (Gly), is also as active as UAG (6-13), illustrating that a substitution based on size preserves the biological activity of UAG (6-13). Overall, these analogs of UAG (6-13) demonstrate that conservative substitutions preserve the biological activity of UAG (6-13).

Further, acetylation of Ser in position 6 (N-terminus) of UAG (6-13) preserves the biological activity of UAG (6-13) and a combination of N-terminus acetylation and substitution of, for example, Pro7 by D-Pro (its D form) results in an analog that also exhibits biological activity. Therefore, strategies aiming at stabilizing the N-terminus of UAG (6-13) to improve its resistance to degradation by for example, exopeptidases and endopeptidases (such as, but not limited to, DPP IV) result in peptides that still exhibit biological activity of UAG (6-13), making them useful for in vivo uses.

The peptides of the present invention, including analogs thereof, can be produced in genetically engineered host cells according to conventional techniques. Suitable host cells are those cell types that can be transformed or transfected with exogenous DNA and grown in culture, and include bacteria, fungal cells, and cultured higher eukaryotic cells. Eukaryotic cells, particularly cultured cells of multicellular organisms, are preferred. Techniques for manipulating cloned DNA molecules and introducing exogenous DNA into a variety of host cells are disclosed at least by Sambrook et al., Molecular Cloning: A Laboratory Manual, 2nd ed., Cold Spring Harbor Laboratory Press, Cold Spring Harbor, N.Y., 1989, and Ausubel et al. (eds.), Current Protocols in Molecular Biology, John Wiley and Sons, Inc., NY., 1987.

In general, a DNA sequence encoding the polypeptide of the present invention is operably linked to other genetic elements required for its expression, generally including a transcription promoter and terminator within an expression vector. The vector will also commonly contain one or more selectable markers and one or more origins of replication, although those skilled in the art will recognize that within certain systems selectable markers may be provided on separate vectors, and replication of the exogenous DNA may be provided by integration into the host cell genome. Selection of promoters, terminators, selectable markers, vectors and other elements is a matter of routine design within the level of ordinary skill in the art. Many such elements are described in the literature and are available through commercial suppliers.

To direct a polypeptide into the secretory pathway of a host cell, a secretory signal sequence (also known as a leader sequence, prepro sequence or pre sequence) may be provided in the expression vector. The secretory signal sequence is joined to the DNA sequence in the correct reading frame. Secretory signal sequences are commonly positioned 5' to the DNA sequence encoding the propeptide of interest, although certain signal sequences may be positioned elsewhere in the DNA sequence of interest (see, e.g., Welch et al., U.S. Pat. No. 5,037,743; Holland et al., U.S. Pat. No. 5,143,830). The methods to produce and/or manufacture the polypeptide of the invention are well known and well practiced in the art.

The peptides of the invention may be synthesized by solid-phase synthesis. Solid-phase synthesis is a common method for synthesizing peptides. Basically, in this technique, molecules are bound on a bead and synthesized step-by-step in a reactant solution; compared with normal synthesis in a liquid state, it is easier to remove excess reactant or by-product from the product. In this method, building blocks are protected at all reactive functional groups. The two functional groups that are able to participate in the desired reaction between building blocks in the solution and on the bead can be controlled by the order of deprotection.

In the basic method of solid-phase synthesis, building blocks that have two function groups are used. One of the functional groups of the building block is usually protected by a protective group. The starting material is a bead which binds to the building block. At first, this bead is added into the solution of the protected building block and stirred. After the reaction between the bead and the protected building block is completed, the solution is removed and the bead is washed. Then the protecting group is removed and the above steps are repeated. After all steps are finished, the synthesized compound is cleaved from the bead.

If a compound containing more than two kinds of building blocks is synthesized, a step is added before the deprotection of the building block bound to the bead; a functional group which is on the bead and did not react with an added building block has to be protected by another protecting group which is not removed at the deprotective condition of the building block. By-products which lack the building block of this step only are prevented by this step. In addition, this step makes it easy to purify the synthesized compound after cleavage from the bead.

Usually, peptides are synthesized from the chain in this method, although peptides are synthesized in the opposite direction in cells. An amino-protected amino acid is bound to a bead (a resin), forming a covalent bond between the carbonyl group and the resin. Then the amino group is deprotected and reacted with the carbonyl group of the next amino-protected amino acid. The bead now bears two amino acids. This cycle is repeated to form the desired peptide chain. After all reactions are complete, the synthesized peptide is cleaved from the bead.

The protecting groups for the amino groups mostly used in this peptide synthesis are, but not limited to 9-fluorenylmethyloxycarbonyl group (Fmoc) and t-butyloxycarbonyl (Boc). The Fmoc group is removed from the amino terminus with base while the Boc group is removed with acid. Any one of skill in the art to which this invention pertains will be familiar with the technique of solid-phase synthesis of peptides.

Other techniques may be used to synthesize the peptides of the invention. The techniques to produce and obtain the peptides of the invention are well known in the art.

The peptides of the invention can be purified using fractionation and/or conventional purification methods and media. For example, ammonium sulfate precipitation and acid or chaotrope extraction may be used for fractionation of samples. Exemplary purification steps may include hydroxyapatite, size exclusion, FPLC and reverse-phase high performance liquid chromatography. Suitable anion exchange media include derivatized dextrans, agarose, cellulose, polyacrylamide, specialty silicas, and the like. PEI, DEAE, QAE and Q derivatives may be used (Pharmacia, Piscataway, N.J.). Exemplary chromatographic media include those media derivatized with phenyl, butyl, or octyl groups, such as Phenyl-Sepharose FF (Pharmacia), Toyopearl butyl 650 (Toso Haas, Montgomeryville, Pa.), Octyl-Sepharose (Pharmacia) and the like; or polyacrylic resins, such as Amberchrom CG 71 (Toso Haas) and the like. Suitable solid supports include glass beads, silica-based resins, cellulosic resins, agarose beads, cross-linked agarose beads, polystyrene beads, cross-linked polyacrylamide resins and the like. These supports may be modified with reactive groups that allow attachment of proteins by amino groups, carboxyl groups, sulfhydryl groups, hydroxyl groups and/or carbohydrate moieties. Examples of coupling chemistries include cyanogen bromide activation, N-hydroxysuccinimide activation, epoxide activation, sulfhydryl activation, hydrazide activation, and carboxyl and amino derivatives for carbodiimide coupling chemistries. These and other solid media are well known and widely used in the art, and are available from commercial suppliers.

Although UAG fragments containing amino acid residues 1-5, 1-14, 1-18, 6-13, 8-12, 8-13, 8-11, 9-11, 9-12, 17-28 and analogs of UAG fragments, have been synthesized, the present invention also provides for any other fragments of SEQ ID NO: 1 and analogs thereof retaining at least one of the biological activities of the full-length UAG. A skilled person in the art, with knowledge of the instant invention, would readily determine if a particular UAG fragment or analog thereof has the expected biological activities.

Therapeutic Uses and Treatments

The expression "treating a disease or a disorder" refers to administering a therapeutic substance effective to ameliorate symptoms associated with a disease, to lessen the severity or cure the disease, or to prevent the disease from occurring.

As used herein, the term "treatment" refers to both therapeutic treatment as well as to prophylactic and preventative measures. Those in need of treatment include those already with the disease or disorder, condition or medical condition as well as those in which the disease, disorder, condition or medical condition is to be prevented. Those in need of treatment are also those in which the disorder, disease, condition or medical condition has occurred and left after-effects or scars. Treatment also refers to administering a therapeutic substance effective to improve or ameliorate symptoms associated with a disease, a disorder, condition or medical condition to lessen the severity of or cure the disease, disorder, condition or medical condition, or to prevent the disease, disorder or condition from occurring.

The term "metabolic disorders" refers to, but is not limited to, disorders of carbohydrate metabolism, disorders of amino acid metabolism, disorders of organic acid metabolism (organic acidurias), disorders of fatty acid oxidation and mitochondrial metabolism, disorders of porphyrin metabolism, disorders of purine or pyrimidine metabolism, disorders of steroid metabolism, disorders of mitochondrial function, disorders of peroxisomal function and lysosomal storage disorders.

The term "metabolic syndrome" refers to a combination of medical disorders that increase one's risk for cardiovascular disease and/or diabetes.

It is thus an aspect of the invention that fragments of unacylated ghrelin and analogs thereof and peptides comprising them have a glucose lowering effect since unacylated ghrelin prevents the hyperglycemic effects of acylated ghrelin, an insulin sensitizing effect, an insulin secretion enhancement effect, a body fat weight lowering effect, a free fatty acids (FFA) and cortisol lowering effect, indicating an effect of fragments of unacylated ghrelin on dyslipidemia. In addition to these properties, fragments of unacylated ghrelin and analogs thereof are capable of stimulating the proliferation and the survival, as well as inhibiting death, of insulin-secreting cells such as, pancreatic β-cells.

The invention thus provides for a therapeutic potential of fragments of unacylated ghrelin and analogs thereof in the treatment of, for example, diabetes, other medical conditions related to impaired glucose or insulin metabolism, insulin deficiencies or resistance, dyslipidemia, obesity, the metabolic syndrome and the treatment of insulin secreting cells such as pancreatic β-cells.

It is a further aspect, the invention provides for any pharmaceutical compositions incorporating at least one of the peptides of the invention, which share the same potential therapeutic indication as UAG itself.

The peptides of the present invention can be used for and can be incorporated in pharmaceutical formulations to be used in the prevention, reduction and/or treatment of for example, but not limited to, disorders or medical conditions associated with impaired glucose metabolism, impaired insulin metabolism, impaired lipid metabolism, type I diabetes, type II diabetes, obesity, dyslipidemia, atherosclerosis, cardiovascular diseases, metabolic syndrome disorders associated with impaired proliferation of insulin-secreting cells or with insulin resistance.

For therapeutic and/or pharmaceutical uses, the peptides of the invention may be formulated for, but not limited to, intravenous, subcutaneous, transdermal, oral, buccal, sublingual, nasal, inhalation, pulmonary, or parenteral delivery according to conventional methods. Intravenous injection may be by bolus or infusion over a conventional period of time. The peptides of the invention may also be compatible with drug delivery system such as, but not limited to, polymer-based depot formulations.

Active ingredients to be administered orally as a suspension can be prepared according to techniques well known in the art of pharmaceutical formulation and may contain, but are not limited to, microcrystalline cellulose for imparting bulk, alginic acid or sodium alginate as a suspending agent, methylcellulose as a viscosity enhancer, and sweeteners/flavoring agents. As immediate release tablets, these compositions may contain, but not limited to microcrystalline cellulose, dicalcium phosphate, starch, magnesium stearate and lactose and/or other excipients, binders, extenders, disintegrants, diluents and lubricants.

Administered by nasal aerosol or inhalation formulations may be prepared, for example, as solutions in saline, employing benzyl alcohol or other suitable preservatives, absorption promoters to enhance bioavailability, employing fluorocarbons, and/or employing other solubilizing or dispersing agents.

The peptides of the invention may be administered in intravenous (both bolus and infusion), intraperitoneal, subcutaneous, topical with or without occlusion, or intramuscular form. When administered by injection, the injectable solution or suspension may be formulated using suitable non-toxic, parenterally-acceptable diluents or solvents, well-known in the art.

In general, pharmaceutical compositions will comprise at least one of the peptides of the invention together with a pharmaceutically acceptable carrier which will be well known to those skilled in the art. The compositions may further comprise for example, one or more suitable excipients, diluents, fillers, solubilizers, preservatives, salts, buffering agents and other materials well known in the art depending upon the dosage form utilised. Methods of composition are well known in the art.

In the present context, the term "pharmaceutically acceptable carrier" is intended to denote any material, which is inert in the sense that it substantially does not have any therapeutic and/or prophylactic effect per se. A pharmaceutically acceptable carrier may be added to the peptides of the invention with the purpose of making it possible to obtain a pharmaceutical composition, which has acceptable technical properties.

Therapeutic dose ranges of the invention will generally vary from about 0.01 μg/kg to about 10 mg/kg. Therapeutic doses that are outside this range but that have the desired therapeutic effects are also encompassed by the present invention.

Suitable dosage regimens are preferably determined taking into account factors well known in the art including, but not limited to, type of subject being dosed; age, weight, sex and medical condition of the subject; the route of administration; the renal and hepatic function of the subject; the desired effect; and the particular compound employed.

For example, a therapeutically effective amount of the peptides of the invention (also referred to herein as "active compound") is an amount sufficient to produce a clinically significant change in lowering blood glucose levels, improving insulin sensitivity and/or secretion, reducing blood free fatty acids levels, lowering body fat weight, decreasing cortisol levels and/or increasing survival of insulin-secreting cells, amongst other changes. The tests for measuring such parameters are known to those of ordinary skill in the art.

The peptides of the invention can be provided in a kit. Such a kit typically comprises an active compound in dosage form for administration. A dosage form comprises a sufficient amount of active compound such that a desirable effect can be obtained. Preferably, a kit comprises instructions indicating the use of the dosage form to achieve the desired effect and the amount of dosage form to be taken over a specified time period.

EXPERIMENTS AND DATA ANALYSIS

UAG Fragments Promote INS-1E β-Cell Survival

Cell survival was assessed by MTT assay in INS-1E rat β-cells incubated with either full length human UAG (1-28) or UAG (1-14), UAG (1-18), UAG (1-5) and UAG (17-28) in serum deprived medium, either alone or with IFN-γ/TNF-α/IL-1β, whose synergism has been shown to be involved in β-cell death in both type 1 and type 2 diabetes (Ref. 16). The peptides were tested at increasing concentrations, ranging from 0.1 nM to 100 nM. In serum-free conditions, UAG (1-14) and (1-18) showed significant survival effect, comparable to that of UAG (1-28). Under the same conditions, UAG (1-5) and UAG (17-28) displayed reduced, although significant, survival action (FIG. 1). In the presence of cytokines, all the peptides significantly increased cell survival at every concentration tested (FIG. 2). However, similarly to serum-free condition, UAG (1-5) and UAG (17-28) displayed reduced effect. Interestingly, UAG (1-14) and also UAG (1-18) showed to be more potent than full length UAG (1-28) (FIG. 2). These results indicate that UAG fragments particularly UAG (1-14) and (1-18), similarly to full length UAG (1-28), are able to counteract β-cell death induced by either serum starvation or treatment with cytokines.

UAG Fragments Promote HIT-T15 β-Cell Survival

MTT experiments were also performed in hamster HIT-T15 β-cells, to test the survival effect of UAG (1-28) or its fragments UAG (1-14), UAG (1-18), UAG (1-5) and UAG (17-28) in serum deprived medium, either alone or with IFN-γ/TNF-α/IL-1β. As for the experiments performed on INS-1E β-cells, the peptides were tested at increasing concentrations, ranging from 0.1 nM to 100 nM. With respect to INS-1E, in HIT-T15 cells the peptides displayed different protective effects against both serum starvation- and cytokine-induced cell death. Indeed, whereas UAG (1-14) and UAG (1-18) significantly increased cell viability under both experimental conditions (FIGS. 3A and 3B), UAG (1-5) slightly increased cell survival only in cytokine-treated cells, whereas UAG (17-28) had no significant effect, at any condition examined (FIGS. 4A and 4B).

The survival effect of UAG (6-13), UAG (8-13), UAG (8-12), UAG (8-11), UAG (9-12) and UAG (9-11) was assessed in cytokine-treated HIT-T15 β-cells. As expected, the cytokines (IFN-γ/TNF-α/IL-1β) strongly reduced cell survival with respect to normal culture conditions (serum containing medium). UAG (6-13), at all the concentrations tested (1 nM to 100 nM) and particularly at 100 nM, potently inhibited cytokine-induced cell death by increasing cell survival up to values similar to or even greater than those observed in the presence of serum. Interestingly, the survival effect of UAG (6-13) was comparable to that of full length UAG (1-28) (FIG. 5A).

Figure 5B:
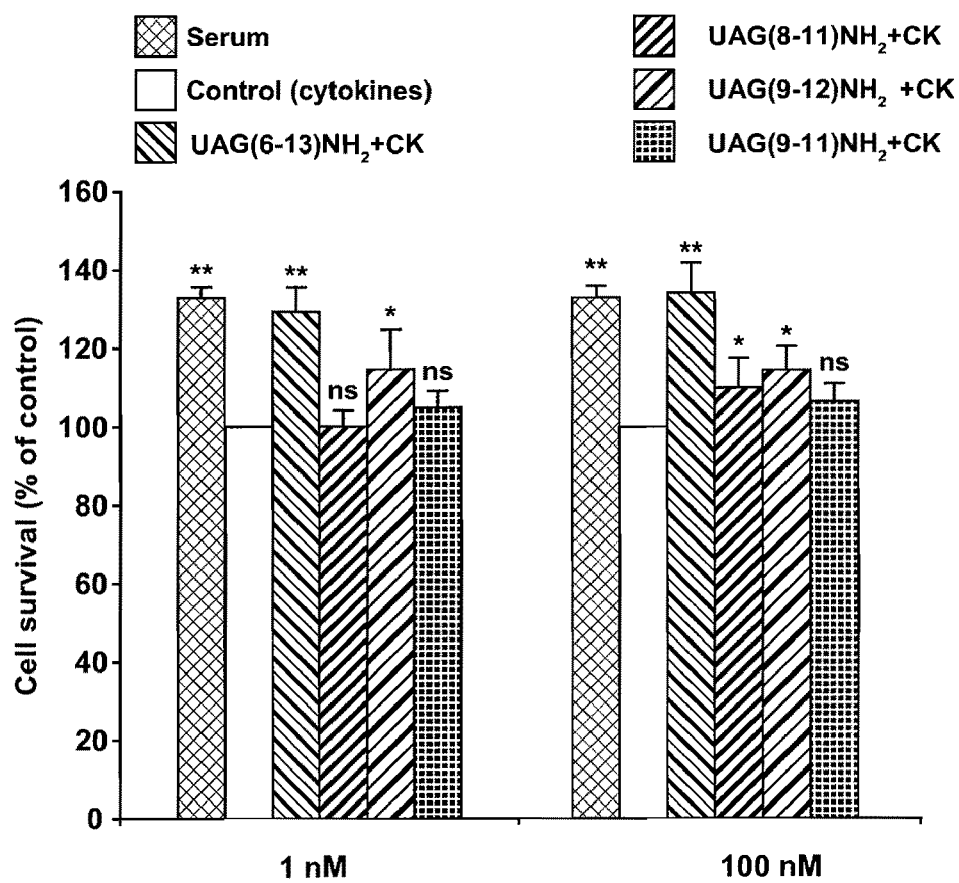

Under the same experimental condition, UAG (8-13), although less than UAG (6-13), showed significant protective effect at all the concentrations examined, whereas UAG (8-12) displayed significant, although reduced protection, only at 10 nM and 100 nM. The protective effects of peptides UAG (8-13) and UAG (8-12) were found similar to those of UAG (1-14) and UAG (1-18). A peptide made of the inverse sequence of UAG (1-14) and named UAG (14-1), was used as negative control for these experiments (FIG. 5A). With regard to UAG (8-11), UAG (9-12) and UAG (9-11) (FIG. 5B), MTT results indicated that UAG (8-11) exerted significant survival effect only at 100 nM and UAG (9-12) significantly increased cell survival at both the concentrations tested (1 and 100 nM). These effects were however lower than those of UAG (6-13) (FIG. 5B). UAG (9-11) had no significant effect at both concentrations tested (FIG. 5B).

UAG Fragments Exert Antiapoptotic Effects in HIT-T15 β-Cells

HIT-T15 β-cells were cultured for 24 h in serum-free medium, either alone or with IFN-γ/TNF-α/IL-1β. In both cell lines, apoptosis increased under cytokine treatment, with respect to serum starvation alone. UAG (6-13) increased the number of cells, induced cell enlargement and small islets formation, with respect to cytokine condition (data not shown). Moreover, it significantly reduced cytokine-induced apoptosis at the concentration of 1 nM, 10 nM and, particularly, at 100 nM where the antiapoptotic effect was even stronger than that displayed by UAG (1-28) (FIG. 6A). UAG (8-13), although less than UAG (6-13), significantly inhibited apoptosis at 10 and 100 nM, whereas UAG (8-12) showed some protective effect only at 100 nM (FIGS. 62 and 6C respectively). UAG (14-1), the inverse sequence of UAG (1-14), was used as negative control, whereas UAG (1-28), was used as positive control in each experiment. These results indicate that, similarly to the results obtained for cell survival, with respect to UAG (8-13) and UAG (8-12), UAG (6-13) exerts the strongest antiapoptotic effect in HIT-T15 β-cells treated with cytokines.

Survival Effect of UAG Fragments in Human Pancreatic Islets

The survival effect of UAG (1-14), UAG (1-18), UAG (1-5) and UAG (17-28), with respect to that of full length UAG (1-28), was assessed in human pancreatic islets by MTT. The peptides were tested in islet cells cultured in serum deprived medium, either alone or with IFN-γ/TNF-α/IL-1β (5 ng/ml each). UAG (1-14) significantly increased cell survival in serum deprived medium at 10 nM and 100 nM, whereas in the presence of cytokines it prevented cell death at 100 nM (FIG. 7A). UAG (1-18) significantly increased cell survival at 1 nM and 10 nM (FIG. 7A). UAG (1-5) displayed little, although significant survival action at 10 nM in serum deprived medium but showed no cell protection after addition of cytokines, at any concentration tested (1 nM to 100 nM) (FIG. 7B). UAG (17-28) significantly increased survival of islet cells cultured in serum deprived conditions, at 10 nM and 100 nM, but had no effect in the presence of cytokines (FIG. 7B). In all, these results indicate that in human islets, UAG (1-14) and UAG (1-18) exert protective effects in serum-free conditions that are similar to those displayed by UAG (1-28), whereas their survival capacity is at least partly lost in cytokine-treated cells where the effect of UAG (1-28) is still evident.

Effect of UAG Fragments on Insulin Secretion in Human Pancreatic Islets

The effects of UAG (1-14) and UAG (1-18), both used at 100 nM, were investigated on insulin secretion in human islets.

Figure 8A:
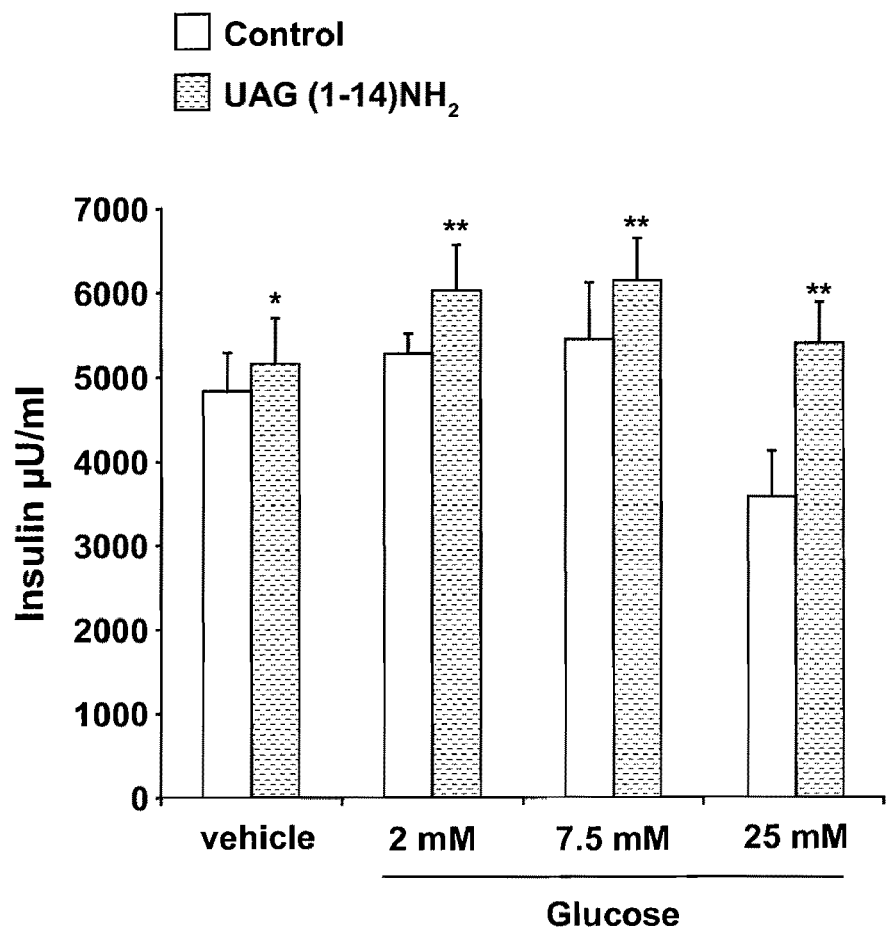
FIGS. 8A to 8D illustrate the effect of UAG (1-14) (FIG. 8A), UAG (1-18) (FIG. 8B), UAG (1-28) (FIG. 8C) and Exendin-4 (FIG. 8D) on insulin secretion in human pancreatic islets.
Figure 8B:
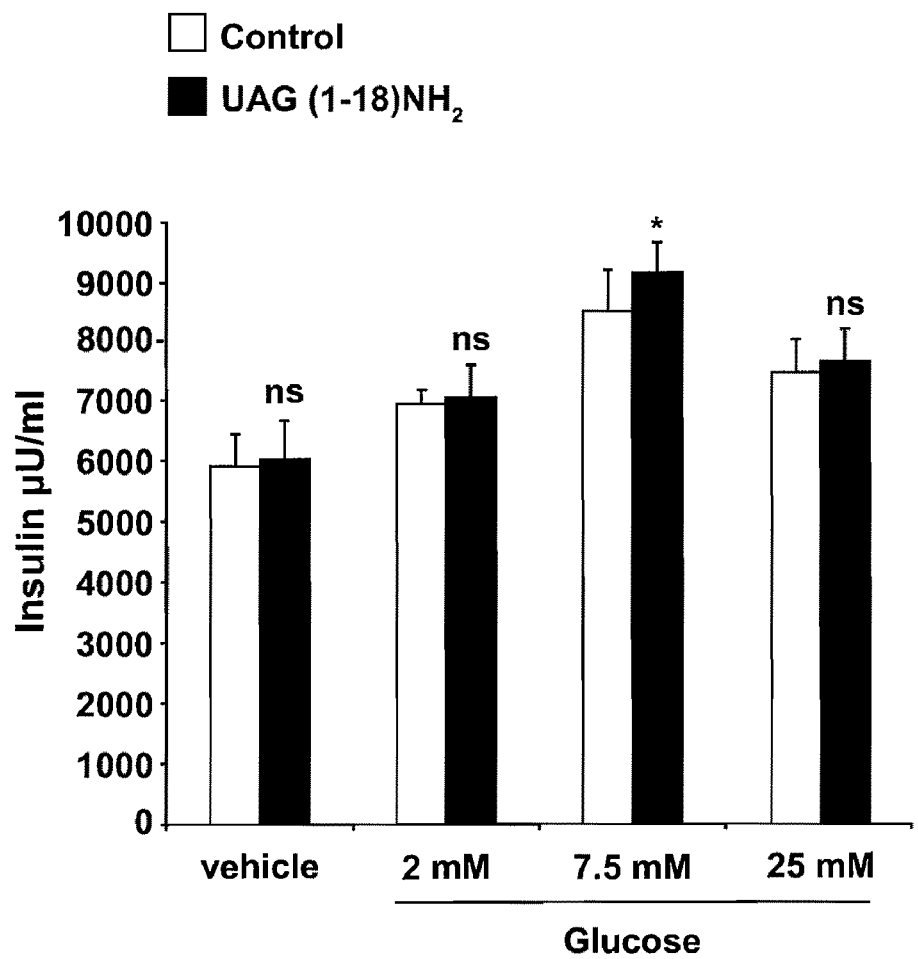
Figure 8C:
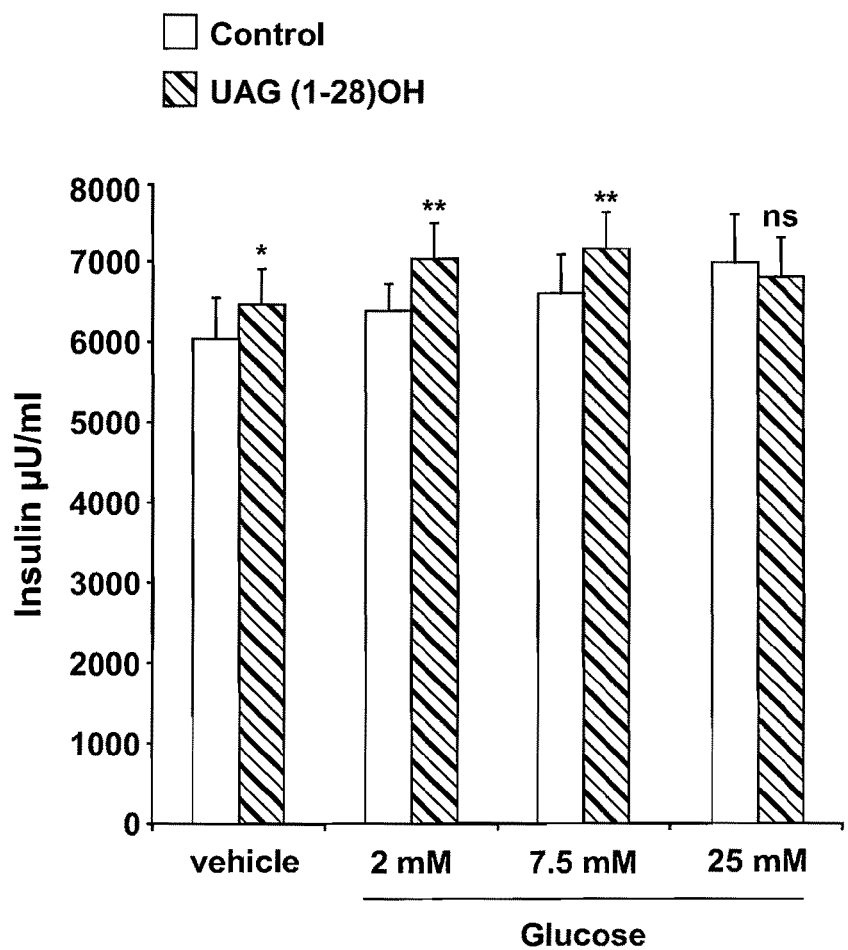
Figure 8D:
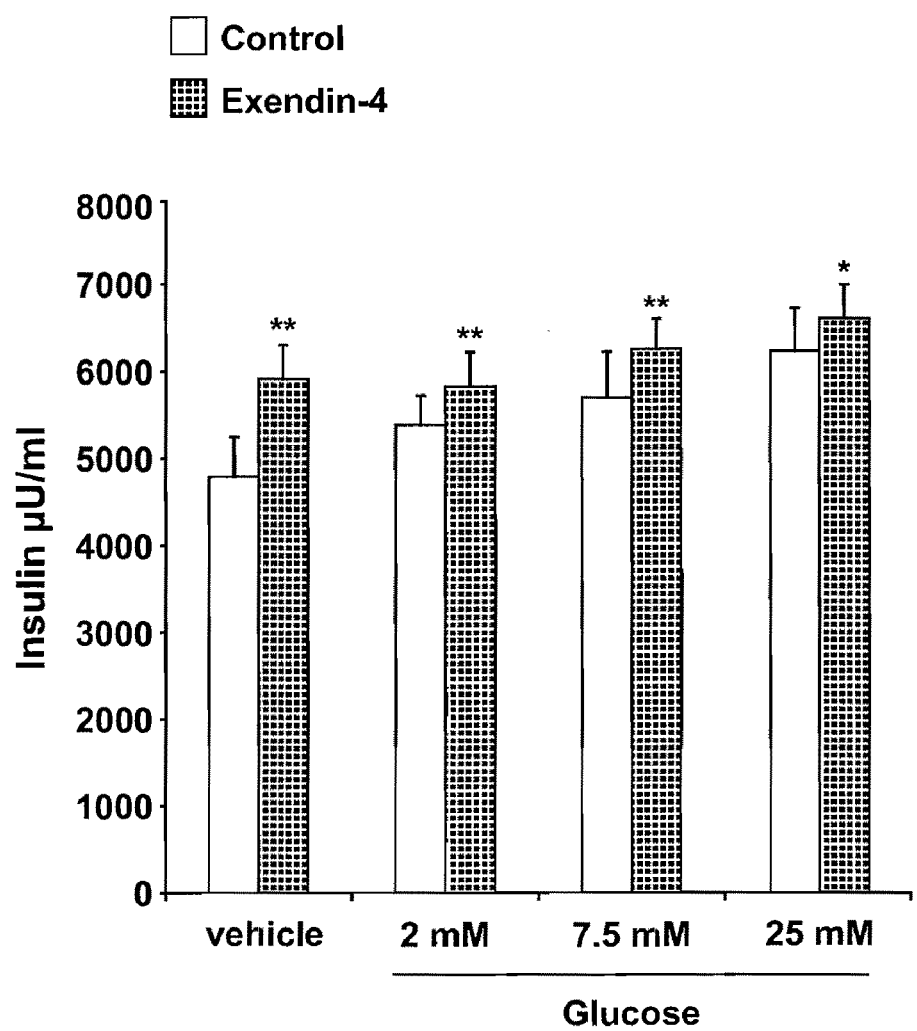

FIG. 8A shows that UAG (1-14), similarly to UAG (1-28) (FIG. 8C) and to exendin-4 (FIG. 8D), significantly increased insulin secretion both in the absence and presence of glucose (2 to 25 mM), whereas UAG (1-18) showed significant effect with 7.5 mM glucose (FIG. 8B). UAG (1-28) and Exendin-4 were used as positive controls (FIGS. 8C and 8D). These results indicate that in human pancreatic islets UAG (1-14) and UAG (1-18) stimulate glucose-induced insulin secretion.

In Vivo Effect of UAG Fragment on Streptozotocin (STZ)-Treated Animals

Figure 9B:
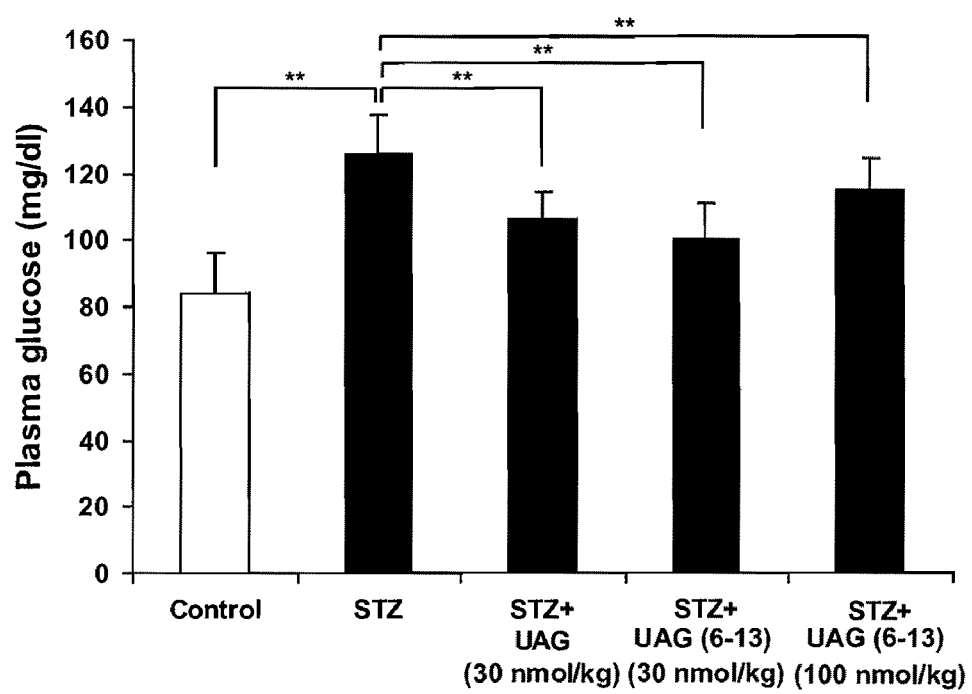
Figure 9C:
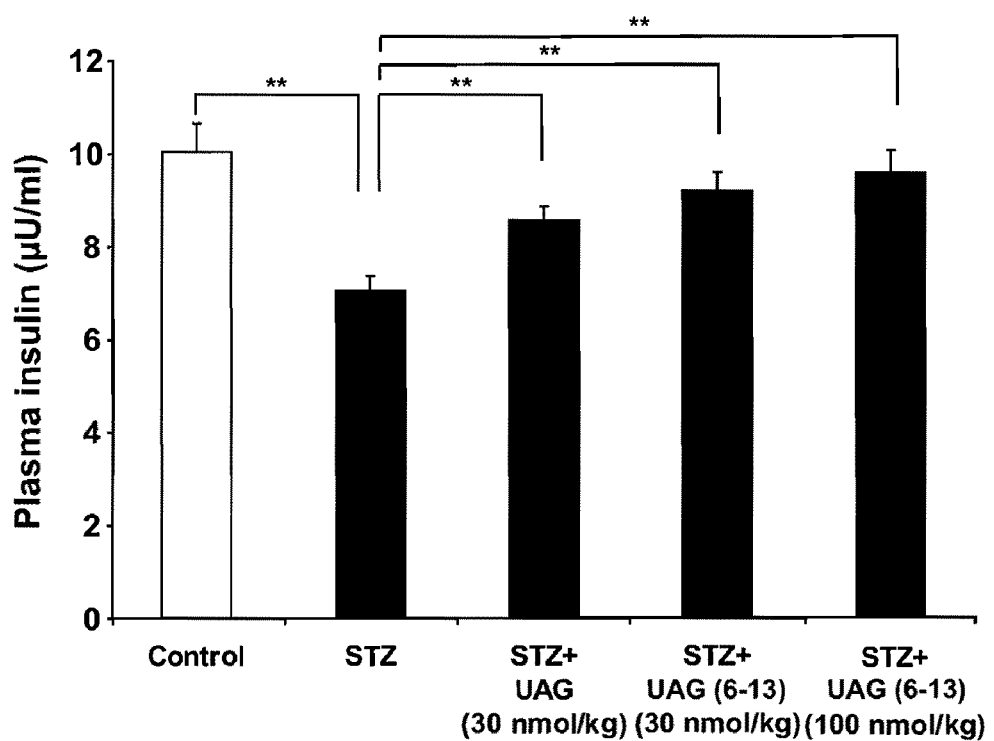
Figure 9D:
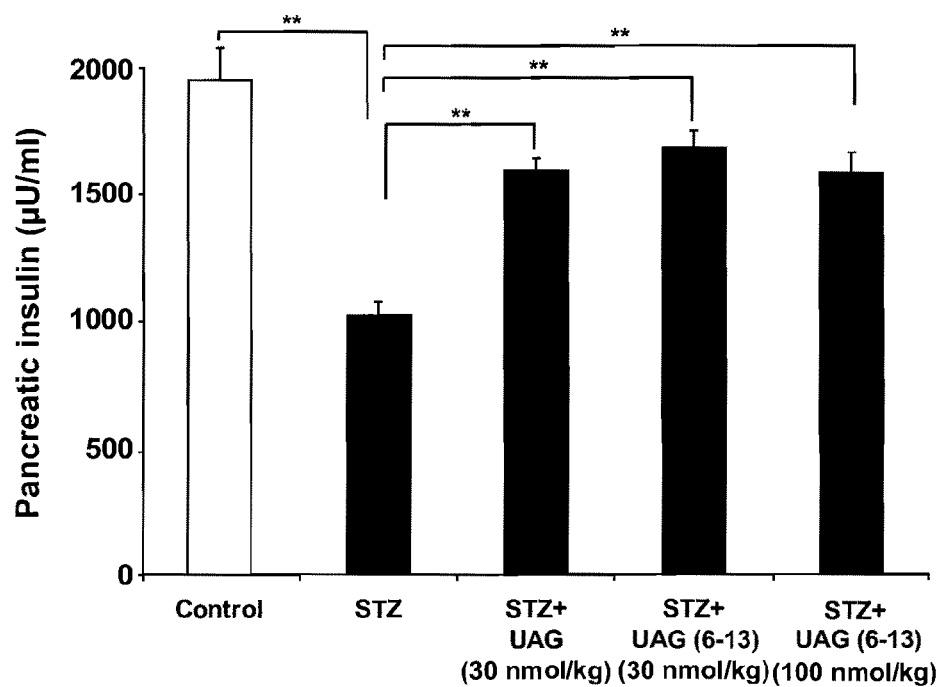

It is well known that Streptozotocin (STZ) treatment in neonatal rats causes diabetes (Refs. 24, 25, 26). Herein, the long-term effects of UAG (6-13) (one week of treatment following STZ administration, assessment at 70 days following STZ administration vs. those of UAG in neonatal rats treated with STZ at day 1 of birth) was investigated. UAG (6-13) was tested at a concentration that was equal (30 nmol/l) or higher (100 nmol/l) than that of UAG. Interestingly, at day 9 after injection with STZ, the animal survival rate, that was decreased by STZ with respect to the Control group (≈52%), was strongly increased by UAG (≈72%), and by both UAG (6-13) concentrations (≈71% and 89% for 30 nmol/l and 100 nmol/l, respectively) (FIG. 9A). At day 70, plasma glucose was significantly increased by 150% (P<0.01) in STZ group with respect to Control. UAG, as expected, counteracted STZ effect by reducing glucose levels (by ≈21%). A similar effect was obtained with both 30 nmol/l and 100 nmol/l UAG (6-13) (reduction of 31% and 14%, respectively vs. STZ group). Interestingly, UAG (6-13) at equal concentration showed an effect that was stronger than that of UAG (FIG. 9B). STZ-treated animals showed significant reduction of plasma insulin levels; UAG, as well as UAG (6-13), at both concentrations, significantly reduced this effect by increasing insulin levels in STZ-treated rats (FIG. 9C). Similar results were obtained with regard to pancreatic insulin secretion (FIG. 9D). These results indicate that at day 70 after treatment with STZ, UAG (6-13), similarly or even more than UAG, is able to reduce STZ-induced plasma glucose increase and to improve both plasma and pancreatic insulin levels.

UAG Fragments Modulate Plasma Glucose Levels, Insulin Sensitivity as Well as Gonadal Fat Weight In Vivo in a Genetic Model of Diabetes Associated with Obesity and Insulin Resistance, the ob/ob Mice Baseline tail vein plasma samples were collected from free-fed and 16 h fasted ob/ob mice 7 and 6 days before pump implantation into $K_2$EDTA coated capillary tubes (Microvette CB300 K2E; Sarstedt, Germany). The animals were then separated into three groups with approximately equivalent weight ranges. Ten week old mice were anesthetized, and a filled Alzet 1004 pump was inserted, delivery portal first, into the peritoneal cavity. The musculoperitoneal and skin layers were then closed using interrupted sutures (Vicryl 5.0 FS-2 absorbable suture). Animals received pumps containing either saline, 10 mg/ml UAG, or 3.5 mg/mL UAG (6-13) (n=8 per group). Alzet 1004 pumps deliver 12 µl/day, and infused 30 µg of hUAG/animal/day (~600 µg/kg/day) and 10 µg of UAG (6-13)/animal/day (~200 µg/kg/day).

Blood samples (at 0900-1000) were obtained from fed and fasted animals at weeks 2 and 4 via the tail vein into EDTA Microvette tubes. Glucose levels in tail vein blood were measured directly using a glucometer. On the last day of treatment baseline (fasted) blood samples were taken.

Figure 14A:
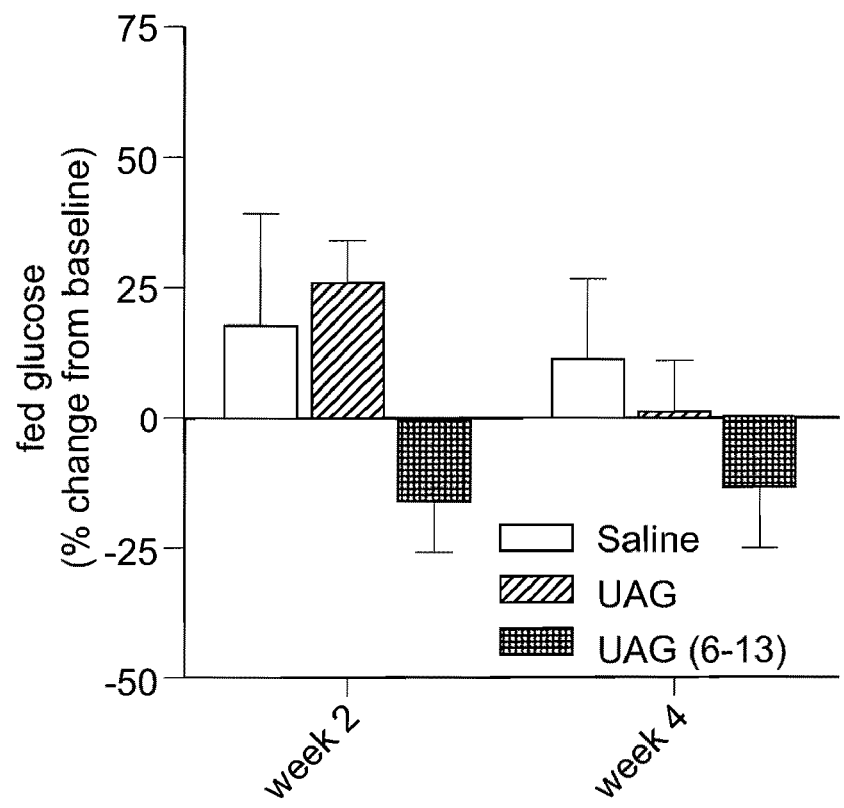
FIGS. 14A and 14B illustrate the in vivo effects of UAG (6-13) on plasma glucose levels after 2 and 4 weeks of treatment in ob/ob mice, an animal model of diabetes associated with obesity.
Figure 14B:
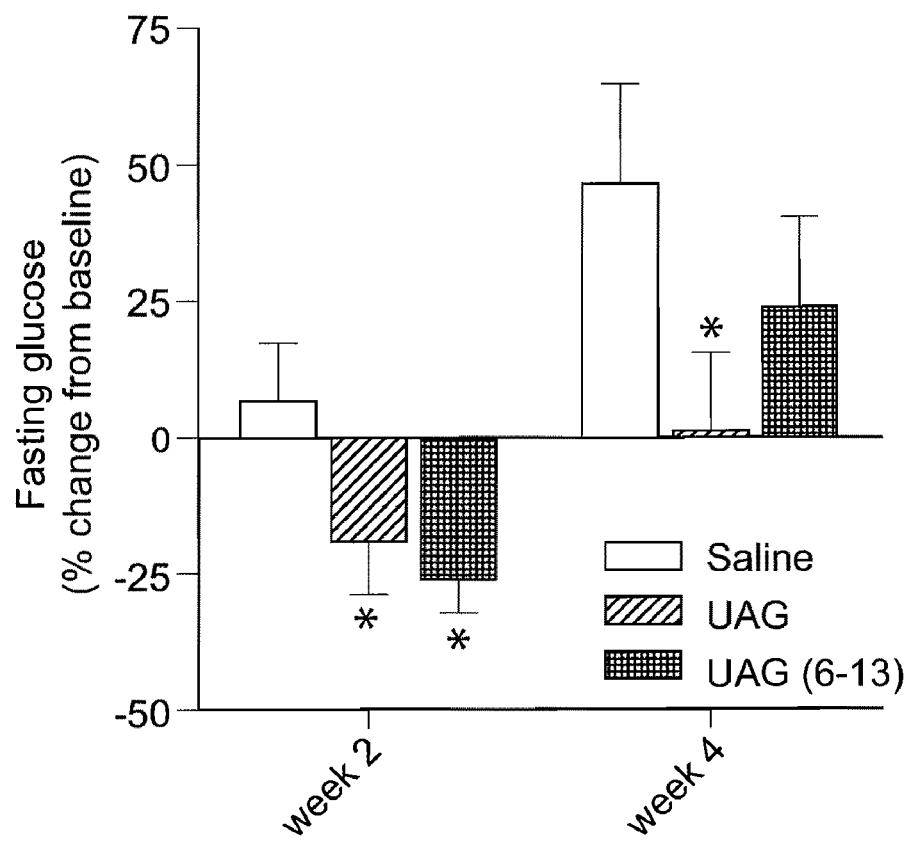

Although no statistically significant effects (RM-ANOVA) were observed on fed plasma glucose levels during the period of treatment, UAG (6-13) showed a consistent suppressive effect relative to saline controls, and by week 4, UAG also suppressed glucose levels relative to controls (FIG. 14A). In contrast, fasting glucose concentrations were significantly suppressed by 25-30% from saline treated controls by UAG and UAG (6-13) treatment at week 2 (FIG. 14B). This effect remained at week 4 (FIG. 14B). As expected, both fasting and fed glucose levels in the controls increased during the period of treatment, since ob/ob mice reach peak hyperglycemia at approximately 12 weeks (Ref. 27).

Figure 15:
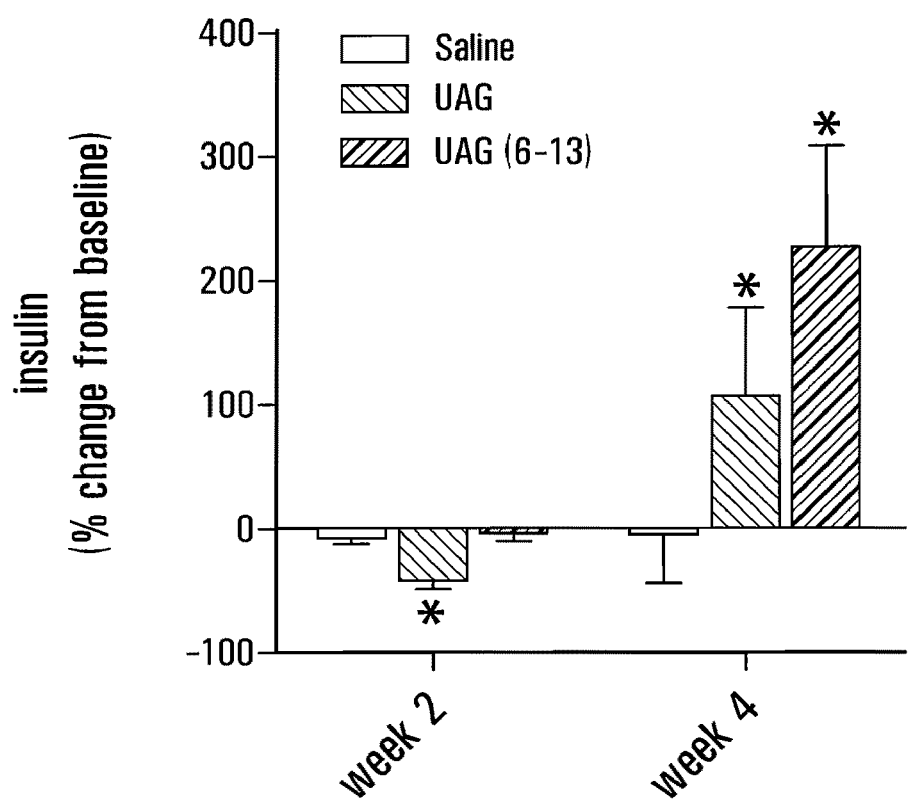
FIG. 15 illustrates fasting insulin levels after 2 and 4 weeks of treatment with UAG and UAG (6-13) in ob/ob mice, an animal model of diabetes associated with obesity.
Figure 16:
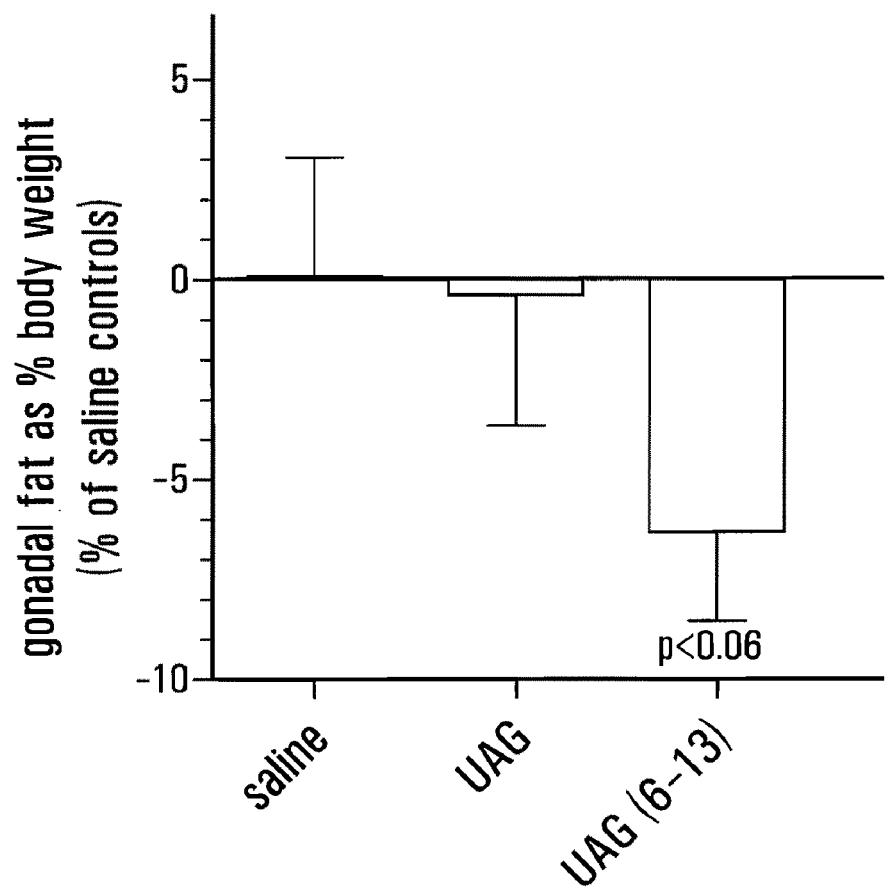
FIG. 16 illustrates the effect of UAG and UAG (6-13) on gonadal fat as percent body weight in ob/ob mice, an animal model of diabetes associated with obesity.

Fasting plasma insulin levels were significantly suppressed by UAG at 2 weeks relative to saline controls (FIG. 15). By 4 weeks of treatment, though, fasting levels of insulin were significantly increased above baseline levels, and relative to saline controls.

During the period of treatment, in UAG (6-13) treated ob/ob animals, gonadal fat pad weight was decreased by approximately 7% relative to saline treated controls (trend p<0.06) (FIG. 16). UAG and UAG (6-13) did not cause an increase in gonadal fat weight over the period of treatment, as is observed with ghrelin treatment. The trend towards a decrease in fat weight suggests that longer exposure to UAG and UAG (6-13) will exert a lipolytic effect translating into a reduction in fat mass, and thus might constitute a promising treatment for obesity, with accompanying beneficial effects on insulin sensitivity (e.g., Refs. 28, 29).

The findings from this long-term treatment protocol were that both UAG and UAG (6-13) suppressed plasma glucose levels in fasted animals after 2 and 4 weeks of treatment, relative to saline control animals. UAG (6-13) also appeared to have a 30-40% suppressive effect on plasma glucose levels in fed animals. The effect of UAG on fasting glucose observed following 2 weeks of treatment corresponded with significantly lowered insulin levels, indicating improved insulin sensitivity.

Binding of UAG Fragments to Pancreatic β-Cell Receptors

Figure 10A:
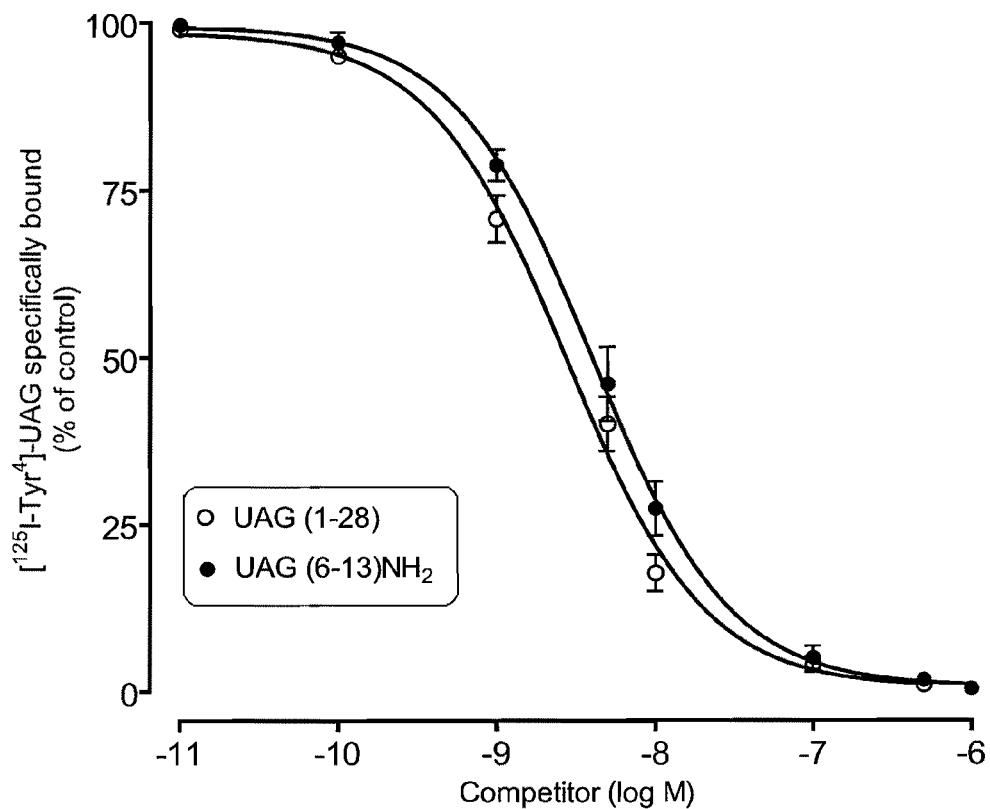
FIGS. 10A and 10B illustrate the binding of unacylated ghrelin and unacylated ghrelin fragment UAG (6-13) to pancreatic HIT-T15 (FIG. 10A) and INS-1E (FIG. 10B) β-cell receptors.
Figure 10B:
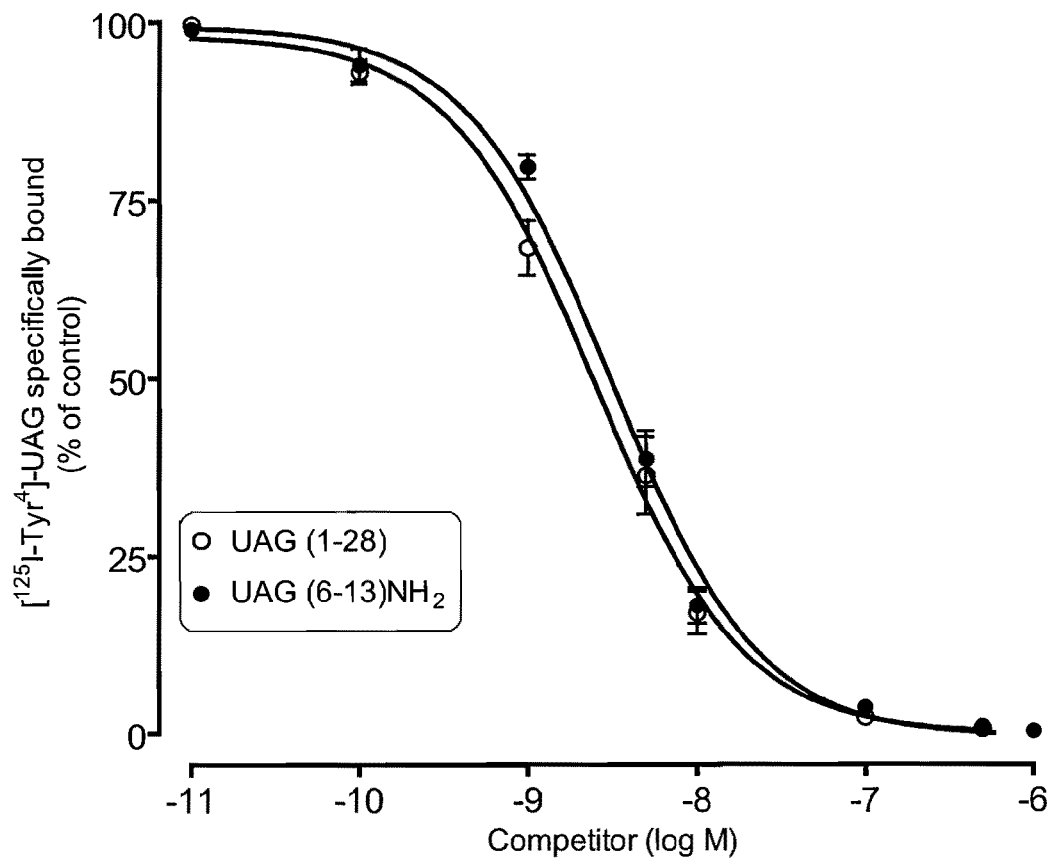

The ability of the fragment UAG (6-13) to compete in a concentration-dependent manner with [$^{125}$I-Tyr$^4$]-UAG for HIT-T15 (FIG. 10A) and INS-1E (FIG. 10B) binding sites was assayed. As shown in FIGS. 10A and 10B, unlabelled UAG (1-28) and UAG (6-13) competed with a similar efficacy and in a concentration-dependent fashion with [$^{125}$I-Tyr$^4$]-UAG for such binding sites in both cell lines. The $IC_{50}$ values calculated from competition binding curves, all expressed as nM concentration, were 2.6±0.5 and 2.0±0.2 for UAG (1-28) and 3.8±0.3 and 2.4±0.3 for UAG (6-13) in HIT-T15 and INS-1E, respectively.

Survival Effects of UAG Fragments with Alanine Substitutions on HIT-T15 β-Cells

Figure 11A:
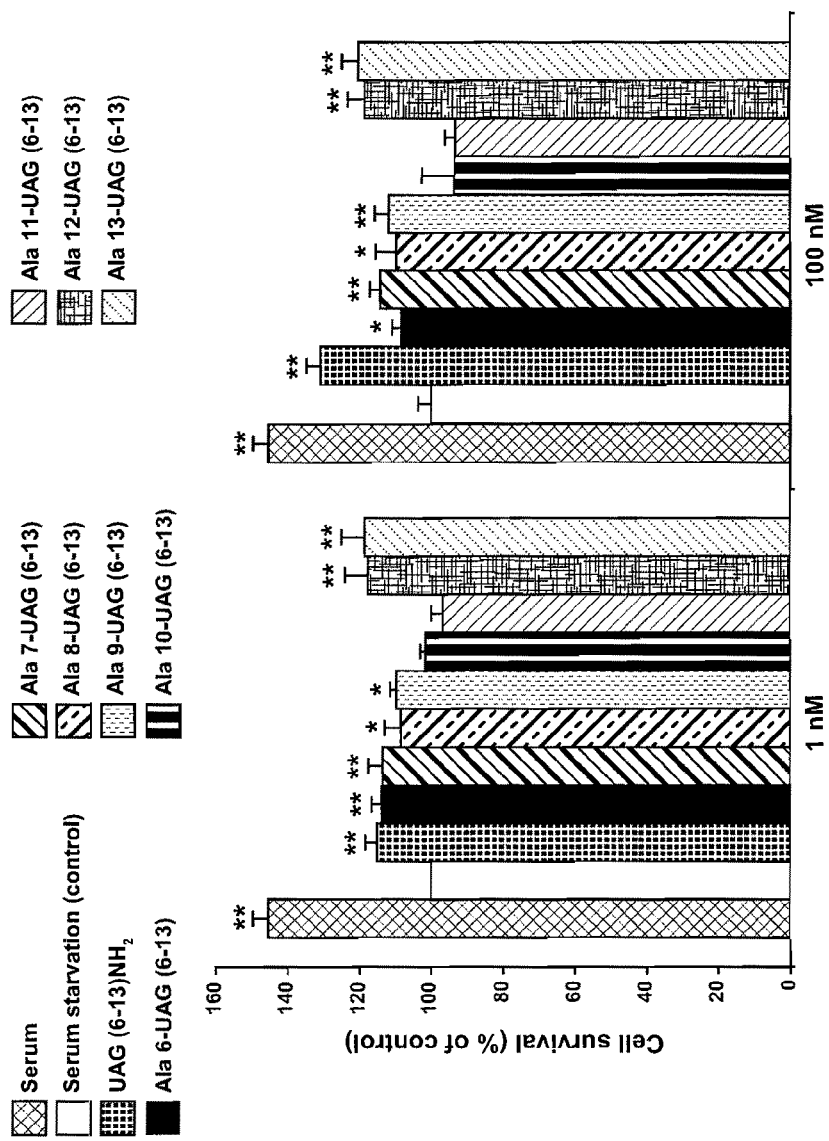
FIGS. 11A and 11B illustrate the survival effects of UAG (6-13) with alanine (Ala) substitutions at positions 6 to 13 in HIT-T15 β-cells in both the absence of serum (FIG. 11A) and in the presence of cytokines (FIG. 11B).
Figure 11B:
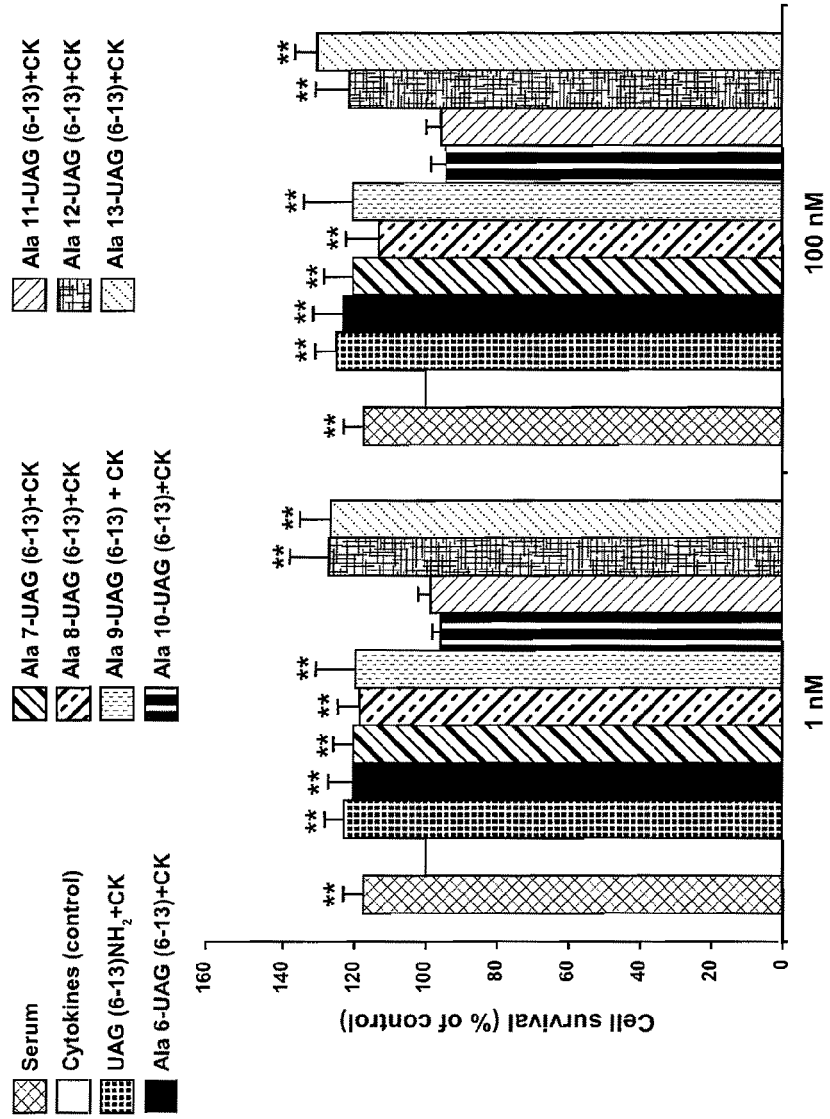

UAG fragments with alanine (Ala) substitutions at different amino acid positions (6 to 13) were tested with regards to their survival effects in HIT-T15 hamster β-cells. The cells were cultured in serum deprived medium, either alone or with IFN-γ/TNF-α/IL-1β. The peptides were tested at the concentrations of 1 nM to 100 nM. In serum-free conditions, where the survival rate was reduced by ≈40% with respect to the presence of serum, UAG (6-13) significantly increased cell survival, as expected (≈18% and ≈30% at 1 and 100 nM, respectively). Ala 6-UAG (6-13), Ala 7-UAG (6-13), Ala 8-UAG (6-13), Ala 9-UAG (6-13) and particularly, Ala 12-UAG (6-13) and Ala 13-UAG (6-13), showed similar effects at both concentrations. By contrast, very low survival effects were displayed by Ala substitution at positions 10 and 11 (FIG. 11A). Under treatment with cytokines, where cell survival was reduced by >18% with respect to serum starved conditions, all Ala substitutions, except those at positions 10 and 11, completely reversed cell death and brought the survival rate to levels that were even higher than those under serum-free conditions, at both 1 nM and 100 nM concentrations. These effects, were similar to those elicited by the original peptide UAG (6-13) (FIG. 11B). Ala substitutions at positions 6 to 9 and 12 to 13 of UAG (6-13) do not affect the peptide survival effect, whereas the side chains of amino acids at position 10 (Q) and 11 (R) seem to play an essential role.

Figure 12A:
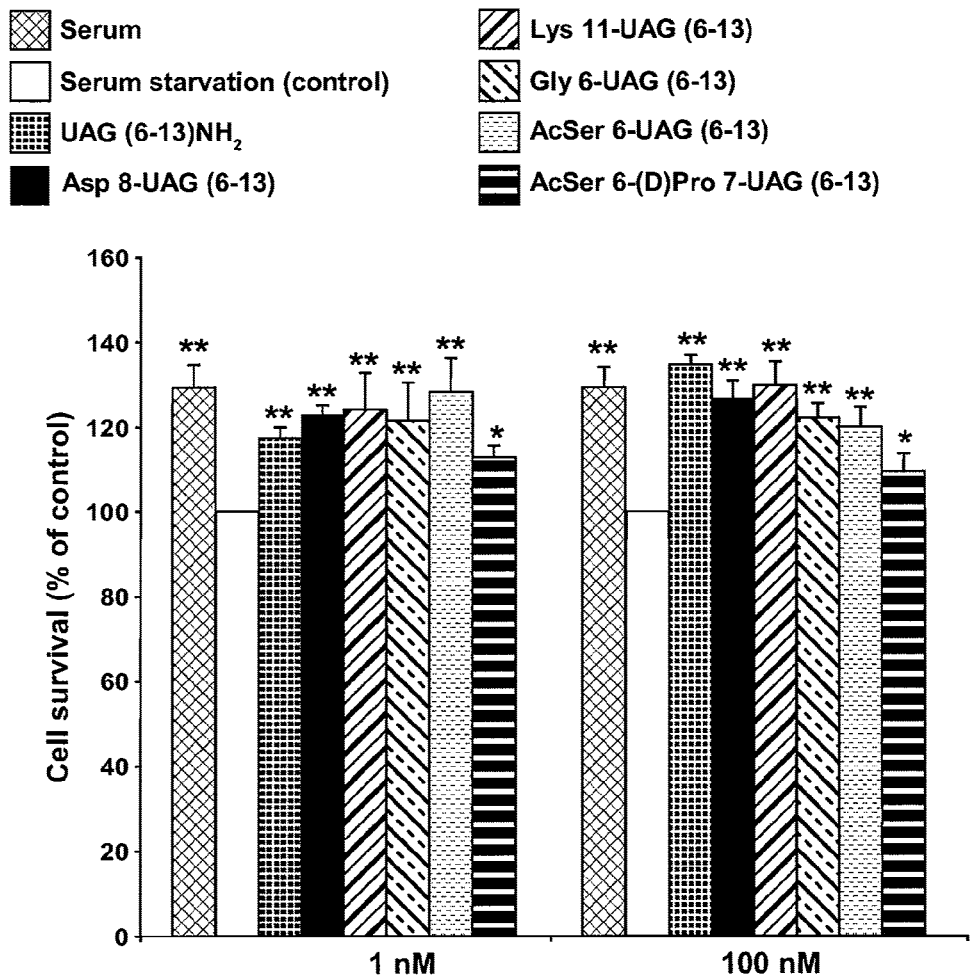
FIGS. 12A and 12B illustrate the survival effects of UAG (6-13) with conservative substitutions and N-terminal modifications in HIT-T15 β-cells, in both the absence of serum (FIG. 12A) and in the presence of cytokines (FIG. 12B).
Figure 12B:
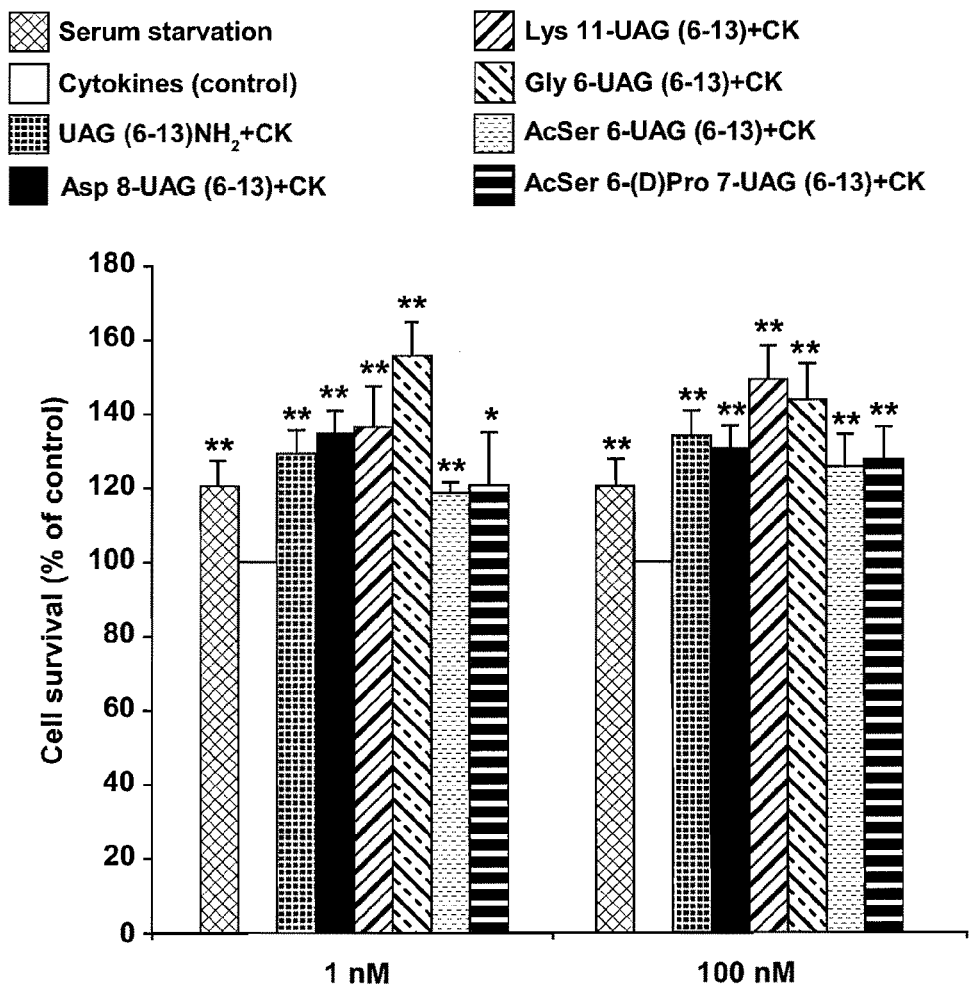

Survival Effects of UAG Fragments with Conservative Substitutions and N-Terminal Modifications on HIT-T15 β-Cells In serum-free conditions, where the survival rate was reduced by ≈35% with respect to the presence of serum, UAG (6-13) significantly increased cell survival, as expected (≈18% and ≈30% at 1 and 100 nM, respectively). Asp 8-UAG (6-13), Lys 11-UAG (6-13), Gly 6-UAG (6-13), as well as AcSer 6-UAG (6-13) and AcSer 6-(D)Pro 7-UAG (6-13) showed similar effects at both concentrations (FIG. 12A). Under the treatment with cytokines, where cell survival was reduced by ≈20%, all the peptides significantly increased cell survival. Particularly, the best effect was exerted by Gly 6-UAG (6-13), whereas the lowest was seen using AcSer 6-UAG (6-13), AcSer 6-(D)Pro 7-UAG (6-13) (FIG. 12B).

Survival Effects of Cyclized UAG Fragments on HIT-T15 β-Cells

Figure 13A:
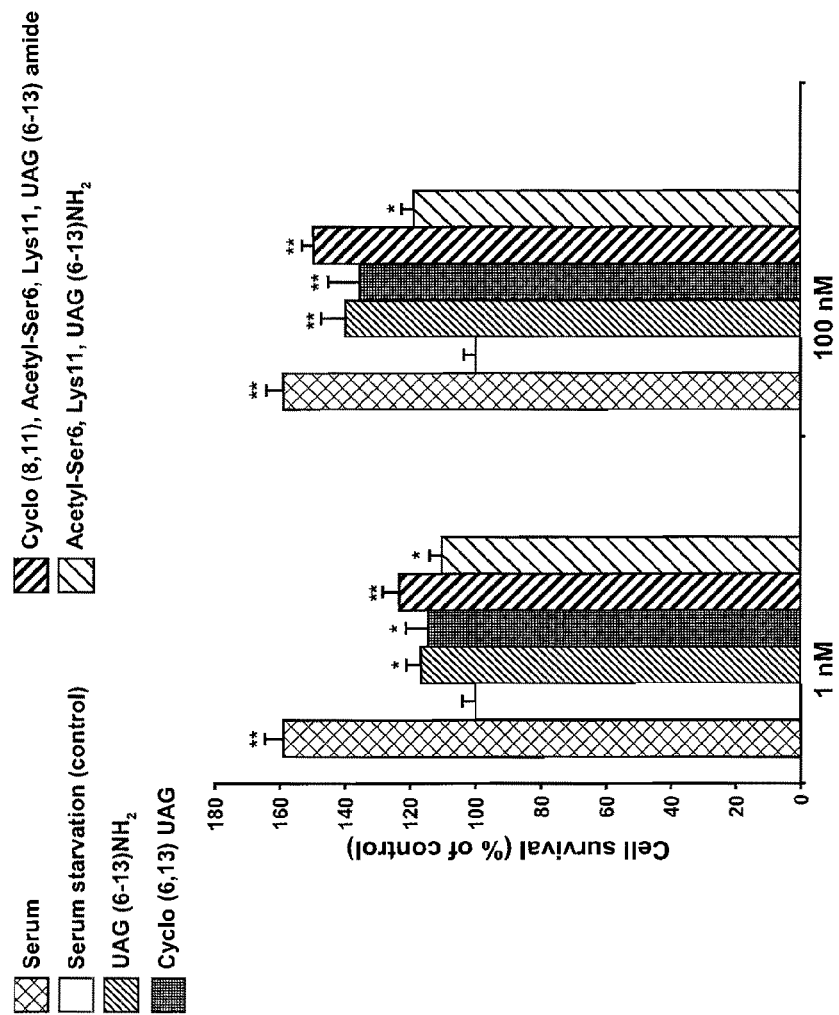
FIGS. 13A and 13B illustrate the survival effects of UAG (6-13) with cyclization in HIT-T15 β-cells in both the absence of serum (FIG. 13A) and in the presence of cytokines (FIG. 13B).
Figure 13B:
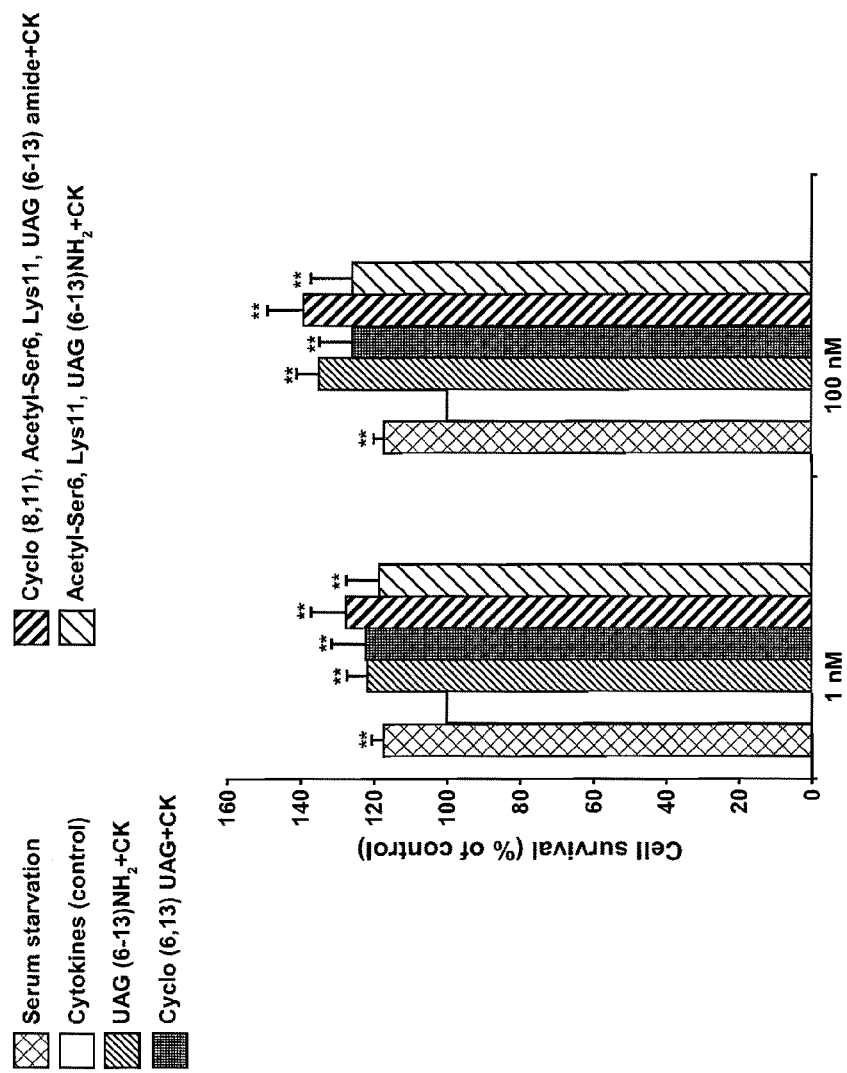

In serum-free conditions, where the survival rate was reduced by ≈58% with respect to the presence of serum, UAG (6-13) significantly increased cell survival, as expected (≈16% and ≈60% at 1 nM and 100 nM, respectively). Cyclo 6,13 UAG (6-13), Cyclo (8,11), Acetyl-Ser6, Lys11, UAG (6-13)amide and Acetyl-Ser6, Lys11, UAG (6-13)$NH_2$ showed similar effects (FIG. 13A). Similar results were found under the treatment with cytokines (FIG. 13B).

Materials and Technical Protocols

Human UAG and UAG fragments (1-14), (1-18), (1-5) and (17-28) as well as exendin-4 were from Phoenix Pharmaceuticals (Belmont, Calif.). The other fragments (6-13), (8-13), (8-12), (8-11), (9-12), (9-11) were from Tib MolBiol (Genova, Italy). Cell culture reagents were from Invitrogen (Milano, Italy). Human UAG (6-13) with alanine (Ala), Ala 6-UAG (6-13), Ala 7-UAG (6-13), Ala 8-UAG (6-13), Ala 9-UAG (6-13), Ala 10-UAG (6-13), Ala 11-UAG (6-13), Ala 12-UAG (6-13) and Ala 13-UAG (6-13) were synthesized by Tib MolBiol (Genova, Italy).

Most of the peptides defined herein were synthesised by means of the simultaneous multiple peptide synthesis on the following instrument: PSSM-8, SHIMADZU, Japan, using the Fmoc/But (G. Schnorrenberg et al. Tetrahedron, 45:7759, 1989) strategy by SHEPPARD (W. C. Chan et al., Fmoc solid phase peptide synthesis—A practical approach, IRL Press, Oxford, 1989). Couplings were performed using 3-6 equiv. Fmoc-amino acid/HOBt/TBTU and 6-12 equiv. N-Methylmorpholine on Tentagel HL RAM resin. The peptides were purified by HPLC instrument SHIMADZU LC-8A. The peptides were deprotected and cleaved from the resin by TFA/water and were characterized by MALDI-TOF by means of a MALDI 2 DE instrument. Finally the peptides were lyophilized in form of the TFA salt.

Cell culture—Hamster HIT-T15 insulin-secreting β-cells were obtained and cultured as described (Refs. 14, 4). INS-1E rat β-cells were kindly provided by Prof. Claes B. Wollheim (University Medical Center, Geneva, Switzerland) and cultured as described (Refs. 14, 4). Cell culture reagents were from Invitrogen (Milano, Italy). Cytokines were from Biosource (Invitrogen, Italy).

Human islet isolation—Human islets were obtained from pancreases of multiorgan donors as described (Ref. 4). Islet preparations with purity>70%, not suitable for transplantation, were provided by European Consortium for Islet Transplantation (ECIT) "Islets for Research Distribution Program," Transplant Unit, Scientific Institute San Raffaele, Vita-Salute University, Milan. Islets (10,000) were cultured in CMRL (Invitrogen) with 10% FBS.

Cell survival assay—Cell survival was assessed by 3-[4,5-dimethylthiazol-2-yl]-2,5 diphenyltetrazolium bromide (MTT) as described previously (Ref. 4). Cells were seeded on 96-well plates at a density of $5 \times 10^3$ cells/well. After treatments, cells were incubated with 1 mg/ml MTT for ~1 h. The medium was aspirated, and the formazan product solubilized with 100 μl DMSO. Viability was assessed by spectrophotometry at 570 nm absorbance using a 96-well plate reader.

Insulin secretion—HIT-T15 cells were plated at density of $5 \times 10^5$ cells into 100-mm dishes and serum starved for 24 h before incubation for 1 h at 37° C. in HEPES-buffered Krebs-Ringer bicarbonate buffer (KRBH), containing 0.5% BSA with 1.25 mM glucose. The medium was changed and the cells were incubated again for 1 h in KRBH/0.5% BSA containing 1.25, 7.5 or 15 mM glucose. Following acid ethanol extraction of the hormone, secreted insulin was quantitated by a radioimmunoassay kit (Linco Research, Labodia, Yens, Switzerland) which recognizes human insulin and cross reacts with rat insulin.

Animals—Pregnant female Sprague-Dawley rats (n=10, day 14th-15th of pregnancy) were purchased from Harlan Srl (Italy), caged allowing free access to water and fed with a standard pellet rat diet. Natural birth occurred 6-7 days later. Five experimental groups were studied: 1) Control group, in which new-born rats received a single i.p. injection of citrate buffer (0.05 mmol/l, pH 4.5); 2) STZ group, which received a single i.p. injection of STZ (100 mg/Kg body weight), freshly dissolved in citrate buffer at day 1 of birth; 3) STZ+UAG group, which received a single i.p. injection of STZ followed by injections of UAG, (30 nmol/kg s.c., twice daily) for 7 days (from day 2 to 8) after birth; 4) STZ+UAG (6-13) group, which received a single i.p. injection of STZ followed by injections of UAG (6-13) (30 nmol/kg s.c., twice daily) for 7 days (from day 2 to 8) after birth; 5) STZ+UAG (6-13) group, which received a single i.p. injection of STZ followed by injections of UAG (6-13), (100 nmol/kg s.c., twice daily) for 7 days (from day 2 to 8) after birth. Dams were randomly assigned to the five groups and pups from the same litter were assigned to the same group. The numbers of dams in each of the four groups 11 (Control), 11 (STZ), 16 (STZ+UAG), and 21 (STZ+UAG (6-13), 30 nmol/kg) and 15 (STZ+UAG (6-13), 100 nmol/kg). Pups were left with their mothers. All neonates were tested on day 2 for glycosuria using Accu-chek compact plus (Roche). Only those animals that were glycosuric at day 2 after birth were included in the STZ model group. Treatments with UAG and UAG (6-13) were started after glycosuria was confirmed. Animals were killed at day 70 after birth by decapitation. Blood samples were collected after decapitation and immediately centrifuged at 20,000×g for 2 min at 4° C., and stored at −20° C. until assayed.

For the experimental data illustrated in FIGS. 14A, 14B, 15 and 16, the animals were obtained from Charles River Laboratories (Maastricht, The Netherlands). Animals (B6.V-Lep$^{ob}$/J, Charles River Laboratories, Belgian colony) were received in our animal facilities at 8 weeks of age, and acclimatized in individual cages for 2 weeks before treatments began. They were maintained under standard 12:12 h light: dark conditions, 21° C., and were allowed free access to food and water. The animals were also handled daily to accustom them to the method used for blood collection. The peptides were dissolved in sterile, nonpyrogenic, 0.9% saline (Baxter BV, Utrecht, The Netherlands). D-glucose was obtained from Sigma-Aldrich Chemie BV (Zwijndrecht, The Netherlands), and was dissolved at 400 mg/ml in 0.9% saline. Alzet pumps (model 1004) were obtained from Charles River Laboratories (Maastricht, The Netherlands). Pumps were filled with 0.9% saline, UAG or UAG (6-13) solution under sterile conditions, and pre-incubated in 0.9% saline for at least 48 hours at 37° C. to initiate flow. Blood glucose levels were measured directly from tail vein incisions using a Freestyle mini glucometer and test strips (ART05214 Rev. A; Abbot, Amersfoort, The Netherlands). Plasma insulin levels were assayed by Ultra-sensitive mouse insulin ELISA (Cat.# 10-1150-10; Mercodia, Sweden).

Pancreas removal and treatment—After excision, pancreases were removed and weighed. For insulin content determination, pancreases (35-50 mg) were homogenized and centrifuged in 5 ml acid-ethanol (0.15 mol/l HCl in 75% [vol/vol] ethanol) at 1,000 g for 20 min; the supernatants were stored at −80° C. For immunohistochemistry, additional pancreases were fixed in 4% paraformaldehyde fixative for 24 h and embedded in paraffin.

Analytical techniques—Plasma glucose levels were determined using a glucose analyzer. Insulin was measured from pancreases or from plasma by RIA as previously described (Ref. 15).

Binding assay—Membranes from hamster HIT-T15 and rat INS-1E pancreatic β-cells were prepared and assayed for the presence of [$^{125}$I-Tyr$^4$]-UAG binding. The ability of UAG fragments to compete with the radioligand for such binding sites has been evaluated as previously described (Ref. 4). Data are presented as mean±S.E.M. of three independent experiments.

Statistical analysis—Results are expressed as means±SE. Statistical analysis were performed using Student's t test or one-way ANOVA. Significance was established when $P<0.05$.

It is understood that the data reported in the present specification are only given to illustrate the invention and may not be regarded as constituting a limitation thereof.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

All published documents mentioned in the above specification are herein incorporated by reference.

REFERENCES

1. Kojima M, Hosoda H, Date Y, Nakazato M, Matsuo H, Kangawa K; (1999) Ghrelin is a growth-hormone-releasing acylated peptide from stomach. Nature 402:656-660.
2. van der Lely A J, Tschop M, Heiman M L, Ghigo E; (2004) Biological, physiological, pathophysiological, and pharmacological aspects of ghrelin. Endocr Rev 25:426-457.
3. Gauna C, Delhanty P J, Hofland L J, Janssen J A, Broglio F, Ross R J, Ghigo E, van der Lely A J; (2005) Ghrelin stimulates, whereas des-octanoyl ghrelin inhibits, glucose output by primary hepatocytes. J Clin Endocrinol Metab 90:1055-1060.
4. Granata R, Settanni F, Biancone L, Trovato L, Nano R, Bertuzzi F, Destefanis S, Annunziata M, Martinetti M, Catapano F, Ghe C, Isgaard J, Papotti M, Ghigo E, Muccioli G; (2007) Acylated and unacylated ghrelin promote proliferation and inhibit apoptosis of pancreatic β cells and human islets involvement of CAMP/PKA, ERK1/2 and PI3K/AKT signaling. Endocrinology 148:512-529.
5. Merglen A, Theander S, Rubi B, Chaffard G, Wollheim C B, Maechler P.; (2004) Glucose sensitivity and metabolism-secretion coupling studied during two-year continuous culture in INS-1E insulinoma cells. Endocrinology 145:667-678.
6. Broglio F, Gottero C, Prodam F, Gauna C, Muccioli G, Papotti M, Abribat T, Van Der Lely A J, Ghigo E; (2004) Non-acylated ghrelin counteracts the metabolic but not the neuroendocrine response to acylated ghrelin in humans. J Clin Endocrinol Metab 89:3062-3065.
7. Asakawa A, Inui A, Fujimiya M et al.; (2005) Stomach regulates energy balance via acylated ghrelin and desacyl ghrelin. Gut 54:18-24.
8. Baldanzi G, Filigheddu N, Cutrupi S, Catapano F, Bonissoni S, Fubini A, Malan D, Baj G, Granata R, Broglio F, Papotti M, Surico N, Bussolino F, Isgaard J, Deghenghi R, Sinigaglia F, Prat M, Muccioli G, Ghigo E, Graziani A; (2002) Ghrelin and des-acyl ghrelin inhibit cell death in cardiomyocytes and endothelial cells through ERK1/2 and PI 3-kinase/AKT. J Cell Biol 159:1029-1037.
9. Date Y, Nakazato M, Hashiguchi S, Dezaki K, Mondal M S, Hosoda H, Kojima M, Kangawa K, Arima T, Matsuo H, Yada T, Matsukura S; (2002) Ghrelin is present in pancreatic alpha-cells of humans and rats and stimulates insulin secretion. Diabetes 51:124-129.
10. Delhanty P J, van Koetsveld P M, Gauna C, van de Zande B, Vitale G, Hofland L J, van der Lely A J; (2007) Ghrelin and its unacylated isoform stimulate the growth of adrenocortical tumor cells via an anti-apoptotic pathway. Am J Physiol Endocrinol Metab. 293:E302-309.
11. Dezaki K, Kakei M, Yada T; (2007) Ghrelin uses Galphai2 and activates voltage-dependent K+ channels to attenuate glucose-induced Ca2+ signaling and insulin release in islet beta-cells: novel signal transduction of ghrelin. Diabetes. 56:2319-2327.
12. Filigheddu N, Gnocchi V F, Coscia M, Cappelli M, Porporato P E, Taulli R, Traini S, Baldanzi G, Chianale F, Cutrupi S, Arnoletti E, Ghè C, Fubini A, Surico N, Sinigaglia F, Ponzetto C, Muccioli G, Crepaldi T, Graziani A; (2007) Ghrelin and des-acyl ghrelin promote differentiation and fusion of C2C12 skeletal muscle cells. Mol Biol Cell. 18:986-994.
13. Gauna C, Kiewiet R M, Janssen J A, van de Zande B, Delhanty P J, Ghigo E, Hofland L J, Themmen A P, van der Lely A J; (2007) Unacylated ghrelin acts as a potent insulin secretagogue in glucose-stimulated conditions. Am J Physiol Endocrinol Metab 293:E697-704.
14. Granata R, Settanni F, Trovato L, Destefanis S, Gallo D, Martinetti M, Ghigo E, Muccioli G; (2006) Unacylated as well as acylated ghrelin promotes cell survival and inhibit apoptosis in HIT-T15 pancreatic beta-cells. J Endocrinol Invest 29:RC19-22.
15. Granata R, Settanni F, Gallo D, Trovato L, Biancone L, Cantaluppi V, Nano R, Annunziata M, Campiglia P, Arnoletti E, Ghè C, Volante M, Papotti M, Muccioli G, Ghigo E; (2008) Obestatin promotes survival of pancreatic β-cells and human islets and induces expression of genes involved in the regulation of -cell mass and function. Diabetes 57:967-79.
16. Mandrup-Poulsen T; (2001) beta-cell apoptosis: stimuli and signaling. Diabetes 50:S58-63.
17. Muccioli G, Pons N, Ghe C, Catapano F, Granata R, Ghigo E; (2004) Ghrelin and des-acyl ghrelin both inhibit isoproterenol-induced lipolysis in rat adipocytes via a non-type 1a growth hormone secretagogue receptor. Eur J Pharmacol 498:27-35.
18. Park S, Dong X, Fisher T L, Dunn S, Omer A K, Weir G, White M F; (2006) Exendin-4 uses Irs2 signaling to mediate pancreatic beta cell growth and function. J Biol Chem 281:1159-1168.
19. Prado C L, Pugh-Bernard A E, Elghazi L, Sosa-Pineda B, Sussel L; (2004) Ghrelin cells replace insulin-producing beta cells in two mouse models of pancreas development. Proc Natl Acad Sci USA 101:2924-2929.
20. Santerre R F, Cook R A, Crisel R M, Sharp J D, Schmidt R J, Williams D C, Wilson C P; (1981) Insulin synthesis in a clonal cell line of simian virus 40-transformed hamster pancreatic beta cells. Proc Natl Acad Sci USA 78:4339-4343.
21. Wajchenberg B L; (2007) beta-cell failure in diabetes and preservation by clinical treatment. Endocr Rev. 28:187-218.
22. Wierup N, Svensson H, Mulder H, Sundler F; (2002) The ghrelin cell: a novel developmentally regulated islet cell in the human pancreas. Regul Pept 107:63-69.
23. Zhang J V, Ren P G, Avsian-Kretchmer O, Luo C W, Rauch R, Klein C, Hsueh A J; (2005) Obestatin, a peptide encoded by the ghrelin gene, opposes ghrelin's effects on food intake. Science 310:996-999.
24. Irako T, Akamizu T, Hosoda H, Iwakura H, Ariyasu H, Tojo K, Tajima N, Kangawa K; (2006) Ghrelin prevents development of diabetes at adult age in streptozotocin-treated newborn rats. Diabetologia 49:1264-1273.
25. Portha B, Levacher C, Picon L, Rosselin G.; (1974) Diabetogenic effect of streptozotocin in the rat during the perinatal period. Diabetes 23:889-895.

26. Tourrel C, Bailbé D, Meile M J, Kergoat M, Portha B; (2001) Glucagon-like peptide-1 and exendin-4 stimulate beta-cell neogenesis in streptozotocin-treated newborn rats resulting in persistently improved glucose homeostasis at adult age. Diabetes 50:1562-1570.
27. Menahan L A; (1983) Age-related changes in lipid and carbohydrate metabolism of the genetically obese mouse. Metabolism 32:172-178.
28. Hayashi T, Boyko E J, McNeely M J, Leonetti D L, Kahn S E, Fujimoto W Y; (2008) Visceral Adiposity, not Abdominal Subcutaneous Fat Area, Is Associated with an Increase in Future Insulin Resistance in Japanese Americans. Diabetes May; 57(5):1269-75. Epub 2008 Feb. 25.
29. Hamdy O, Porramatikul S, Al-Ozairi E; (2006) Metabolic obesity: the paradox between visceral and subcutaneous fat. Curr Diabetes Rev 2:367-373.

The invention claimed is:

1. An isolated polypeptide consisting of a fragment of unacylated ghrelin as set forth in SEQ ID NO: 1, said fragment being 5-18 amino acids in length and comprising amino acid sequence Glu-His-Gln-Arg-Val as set forth in SEQ ID NO: 8 or an analog thereof and having an activity selected from the group consisting of a) decreasing blood glucose levels; b) increasing insulin secretion and/or sensitivity; c) binding to insulin-secreting cells; and d) promoting survival of insulin-secreting cells; and wherein said polypeptide does not comprise an amino acid sequence consisting of amino acids Gly-Ser-Ser-Phe.

2. The isolated polypeptide of claim 1, wherein said polypeptide comprises amino acid sequence Glu-His-Gln-Arg-Val-Gln as set forth in SEQ ID NO: 7 or an analog thereof.

3. The isolated polypeptide of claim 1, wherein said polypeptide comprises amino acid sequence Ser-Pro-Glu-His-Gln-Arg-Val-Gln as set forth in SEQ ID NO: 6 or an analog thereof.

4. The isolated polypeptide of claim 1, wherein said polypeptide comprises amino acid sequence Ser-Pro-Glu-His-Gln-Arg-Val-Gln-Gln-Arg-Lys-Glu-Ser as set forth in SEQ ID NO: 9 or an analog thereof.

5. The isolated polypeptide of claim 4 consisting of any consecutive 5 amino acid residues of the amino acid sequence Ser-Pro-Glu-His-Gln-Arg-Val-Gln-Gln-Arg-Lys-Glu-Ser as set forth in SEQ ID NO: 9.

6. The isolated polypeptide of claim 1, wherein said polypeptide consists of an amino acid sequence selected from the group consisting of Glu-His-Gln-Arg-Val as set forth in SEQ ID NO: 8, Glu-His-Gln-Arg-Val-Gln as set forth in SEQ ID: NO 7, Ser-Pro-Glu-His-Gln-Arg-Val-Gln as set forth in SEQ ID NO: 6, Ser-Pro-Glu-His-Gln-Arg-Val-Gln-Gln-Arg-Lys-Glu-Ser as set forth in SEQ ID NO: 9.

7. The isolated polypeptide of claim 1, wherein said polypeptide consists of a fragment having 5, 6, 7, 8, 9, 10, 11, 12, 13, 14, 15, 16, 17 or 18 amino acids.

8. A method for treating a disorder associated with increased blood glucose levels in a patient comprising administering to the patient a therapeutically effective amount of the polypeptide of claim 1.

9. The method of claim 8, wherein the disorder is diabetes.

10. The method of claim 9, wherein the diabetes is type 1 diabetes.

11. The method of claim 9, wherein the diabetes is type 2 diabetes.

12. The method of claim 8, wherein the disorder is a medical condition associated with insulin deficiencies.

13. The method of claim 8, wherein the disorder is a medical condition associated with dyslipidemia.

14. The method of claim 8, wherein the disorder is a medical condition associated with obesity.

15. The method of claim 8, wherein the disorder is a medical condition related to metabolic syndrome.

16. The method of claim 8, wherein the treatment is through enhancement of proliferation or of survival of the pancreatic β-cells.

17. The method of claim 8, wherein the polypeptide is administered through a route selected from the group consisting of intravenous, subcutaneous, transdermal, oral, buccal, sublingual, nasal delivery and inhalation.

18. The method of claim 8, wherein the polypeptide is administered in a dose varying from about 0.01 µg/kg to about 10 mg/kg.

19. A method of treating insulin resistance in a patient comprising administering to the patient a therapeutically effective amount of the polypeptide of claim 1.

20. The method of claim 19, wherein said polypeptide comprises amino acid sequence Ser-Pro-Glu-His-Gln-Arg-Val-Gln as set forth in SEQ ID NO: 6 or an analog thereof.

21. The isolated polypeptide of claim 1, for treating a disorder associated with increased blood glucose metabolism in a patient.

22. The isolated polypeptide of claim 21, wherein the disorder is type II diabetes.

23. The isolated polypeptide of claim 21, wherein the disorder is obesity.

24. A pharmaceutical composition for treating a disorder associated with increased blood glucose levels comprising a therapeutically effective amount of the isolated polypeptide of claim 1.

25. The isolated polypeptide of claim 1 wherein the polypeptide is cyclized.

26. The isolated polypeptide of claims 1 wherein the polypeptide is linked to a linker moiety.

27. An isolated polypeptide consisting of an amino acid sequence selected from the group consisting of SEQ ID NO: 6, SEQ ID NO: 7, SEQ ID NO: 8, SEQ ID NO: 9, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28.

28. An isolated polypeptide consisting of an amino acid sequence as set forth in SEQ ID NO: 6 and wherein the polypeptide is cyclized.

* * * * *

SEQUENCE LISTING

```
<160> NUMBER OF SEQ ID NOS: 30

<210> SEQ ID NO 1
<211> LENGTH: 28
<212> TYPE: PRT
<213> ORGANISM: Homo sapiens

<400> SEQUENCE: 1

Gly Ser Ser Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 2
<211> LENGTH: 14
<212> TYPE: PRT
<213> ORGANISM: Homo sapiens

<400> SEQUENCE: 2

Gly Ser Ser Phe Leu Ser Pro Glu His Gln Arg Val Gln Gln
1               5                   10

<210> SEQ ID NO 3
<211> LENGTH: 18
<212> TYPE: PRT
<213> ORGANISM: Homo sapiens

<400> SEQUENCE: 3

Gly Ser Ser Phe Leu Ser Pro Glu His Gln Arg Val Gln Gln Arg Lys
1               5                   10                  15

Glu Ser

<210> SEQ ID NO 4
<211> LENGTH: 5
<212> TYPE: PRT
<213> ORGANISM: Homo sapiens

<400> SEQUENCE: 4

Gly Ser Ser Phe Leu
1               5

<210> SEQ ID NO 5
<211> LENGTH: 12
<212> TYPE: PRT
<213> ORGANISM: Homo sapiens

<400> SEQUENCE: 5

Glu Ser Lys Lys Pro Pro Ala Lys Leu Gln Pro Arg
1               5                   10

<210> SEQ ID NO 6
<211> LENGTH: 8
<212> TYPE: PRT
<213> ORGANISM: Homo sapiens
```

```
<400> SEQUENCE: 6

Ser Pro Glu His Gln Arg Val Gln
1               5

<210> SEQ ID NO 7
<211> LENGTH: 6
<212> TYPE: PRT
<213> ORGANISM: Homo sapiens

<400> SEQUENCE: 7

Glu His Gln Arg Val Gln
1               5

<210> SEQ ID NO 8
<211> LENGTH: 5
<212> TYPE: PRT
<213> ORGANISM: Homo Sapiens

<400> SEQUENCE: 8

Glu His Gln Arg Val
1               5

<210> SEQ ID NO 9
<211> LENGTH: 13
<212> TYPE: PRT
<213> ORGANISM: Homo sapiens

<400> SEQUENCE: 9

Ser Pro Glu His Gln Arg Val Gln Gln Arg Lys Glu Ser
1               5                   10

<210> SEQ ID NO 10
<211> LENGTH: 4
<212> TYPE: PRT
<213> ORGANISM: Homo sapiens

<400> SEQUENCE: 10

Glu His Gln Arg
1

<210> SEQ ID NO 11
<211> LENGTH: 4
<212> TYPE: PRT
<213> ORGANISM: Homo sapiens

<400> SEQUENCE: 11

His Gln Arg Val
1

<210> SEQ ID NO 12
<211> LENGTH: 8
<212> TYPE: PRT
<213> ORGANISM: Homo sapiens

<400> SEQUENCE: 12

Ser Pro Asp His Gln Arg Val Gln
1               5

<210> SEQ ID NO 13
<211> LENGTH: 8
<212> TYPE: PRT
<213> ORGANISM: Homo sapiens

<400> SEQUENCE: 13
```

```
Ser Pro Glu His Gln Lys Val Gln
1               5

<210> SEQ ID NO 14
<211> LENGTH: 8
<212> TYPE: PRT
<213> ORGANISM: Homo sapiens

<400> SEQUENCE: 14

Gly Pro Glu His Gln Arg Val Gln
1               5

<210> SEQ ID NO 15
<211> LENGTH: 8
<212> TYPE: PRT
<213> ORGANISM: Homo sapiens

<400> SEQUENCE: 15

Ala Pro Glu His Gln Arg Val Gln
1               5

<210> SEQ ID NO 16
<211> LENGTH: 8
<212> TYPE: PRT
<213> ORGANISM: Homo sapiens

<400> SEQUENCE: 16

Ser Ala Glu His Gln Arg Val Gln
1               5

<210> SEQ ID NO 17
<211> LENGTH: 8
<212> TYPE: PRT
<213> ORGANISM: Homo sapiens

<400> SEQUENCE: 17

Ser Pro Ala His Gln Arg Val Gln
1               5

<210> SEQ ID NO 18
<211> LENGTH: 8
<212> TYPE: PRT
<213> ORGANISM: Homo sapiens

<400> SEQUENCE: 18

Ser Pro Glu Ala Gln Arg Val Gln
1               5

<210> SEQ ID NO 19
<211> LENGTH: 8
<212> TYPE: PRT
<213> ORGANISM: Homo sapiens

<400> SEQUENCE: 19

Ser Pro Glu His Ala Arg Val Gln
1               5

<210> SEQ ID NO 20
<211> LENGTH: 8
<212> TYPE: PRT
<213> ORGANISM: Homo sapiens

<400> SEQUENCE: 20

Ser Pro Glu His Gln Ala Val Gln
1               5
```

```
<210> SEQ ID NO 21
<211> LENGTH: 8
<212> TYPE: PRT
<213> ORGANISM: Homo sapiens

<400> SEQUENCE: 21

Ser Pro Glu His Gln Arg Ala Gln
1               5

<210> SEQ ID NO 22
<211> LENGTH: 8
<212> TYPE: PRT
<213> ORGANISM: Homo sapiens

<400> SEQUENCE: 22

Ser Pro Glu His Gln Arg Val Ala
1               5

<210> SEQ ID NO 23
<211> LENGTH: 8
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: ACETYLATION

<400> SEQUENCE: 23

Ser Pro Glu His Gln Arg Val Gln
1               5

<210> SEQ ID NO 24
<211> LENGTH: 8
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(2)
<223> OTHER INFORMATION: D-amino acid

<400> SEQUENCE: 24

Ser Pro Glu His Gln Arg Val Gln
1               5

<210> SEQ ID NO 25
<211> LENGTH: 8
<212> TYPE: PRT
<213> ORGANISM: Homo sapiens
<220> FEATURE:
<221> NAME/KEY: MISC_FEATURE
<222> LOCATION: (1)..(8)
<223> OTHER INFORMATION: Cyclic

<400> SEQUENCE: 25

Ser Pro Glu His Gln Arg Val Gln
1               5

<210> SEQ ID NO 26
<211> LENGTH: 8
<212> TYPE: PRT
<213> ORGANISM: Homo sapiens
<220> FEATURE:
<221> NAME/KEY: MISC_FEATURE
<222> LOCATION: (3)..(6)
<223> OTHER INFORMATION: Cyclic
```

```
<400> SEQUENCE: 26

Ser Pro Glu His Gln Lys Val Gln
1               5

<210> SEQ ID NO 27
<211> LENGTH: 8
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: ACETYLATION
<220> FEATURE:
<221> NAME/KEY: misc_feature
<222> LOCATION: (3)..(6)
<223> OTHER INFORMATION: Cyclic

<400> SEQUENCE: 27

Ser Pro Glu His Gln Lys Val Gln
1               5

<210> SEQ ID NO 28
<211> LENGTH: 8
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: ACETYLATION

<400> SEQUENCE: 28

Ser Pro Glu His Gln Lys Val Gln
1               5

<210> SEQ ID NO 29
<211> LENGTH: 4
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: ACYLATION

<400> SEQUENCE: 29

Gly Ser Ser Phe
1

<210> SEQ ID NO 30
<211> LENGTH: 4
<212> TYPE: PRT
<213> ORGANISM: Homo sapiens

<400> SEQUENCE: 30

Gly Ser Ser Phe
1
```